United States Patent

Ueno et al.

[11] Patent Number: 6,072,042
[45] Date of Patent: Jun. 6, 2000

[54] BIS(AMINOCARBONYLNAPHTHOL) DERIVATIVE

[75] Inventors: Ryuzo Ueno, Nishinomiya; Masaya Kitayama, Takarazuka; Kenji Minami, Sennan; Hiroyuki Wakamori, Hyogo; Katsunori Tanikawa; Mariko Tanigawa, both of Nishinomiya, all of Japan

[73] Assignee: Kabushiki Kaisha Ueno Seiyaku Oyo Kenkyujo, Osaka, Japan

[21] Appl. No.: 09/077,919

[22] PCT Filed: Oct. 9, 1997

[86] PCT No.: PCT/JP97/03638

§ 371 Date: Jun. 5, 1998

§ 102(e) Date: Jun. 5, 1998

[87] PCT Pub. No.: WO98/16498

PCT Pub. Date: Apr. 23, 1998

[30] Foreign Application Priority Data

Oct. 14, 1996 [JP] Japan ................................. 8-270860

[51] Int. Cl.$^7$ ............... C07C 235/66; C07C 231/02; C07D 271/10; C07D 403/12

[52] U.S. Cl. .................. 534/853; 534/854; 534/820; 534/811; 548/145; 548/305.4; 562/451; 562/455; 564/153

[58] Field of Search .................... 534/820, 853, 534/854; 548/145, 305.4; 562/451, 455; 564/153

[56] References Cited

U.S. PATENT DOCUMENTS

| | | | |
|---|---|---|---|
| 1,579,121 | 3/1926 | Krizikalla et al. | 534/820 X |
| 2,195,443 | 4/1940 | Benade | 534/820 X |
| 5,071,967 | 12/1991 | Hari et al. | 534/820 X |
| 5,298,609 | 3/1994 | Hari | 534/820 X |

FOREIGN PATENT DOCUMENTS

| | | |
|---|---|---|
| 7-238231 | 9/1995 | Japan . |
| 8-087124 | 4/1996 | Japan . |

*Primary Examiner*—Fiona T. Powers
*Attorney, Agent, or Firm*—Sughrue, Mion, Zinn, Macpeak & Seas, PLLC

[57] ABSTRACT

The present invention provides a bis(aminocarbonylnaphthol) derivative which is useful as a raw material for novel azo pigments by bisamidation of each one carboxyl group of two 2-hydroxynaphthalene-3,6-dicarboxylic acids using an aliphatic or aromatic diamine.

4 Claims, 16 Drawing Sheets

BIS(AMINOCARBONYLNAPHTHOL) DERIVATIVE

TECHNICAL FIELD

The present invention relates to a bis (aminocarbonylnaphthol) derivative which is useful as a raw material of an azo compound, and a process for producing the same.

BACKGROUND OF THE INVENTION

Recently, novel pigments and dyes have been developed, intensively, in order to improve paint, ink and photosensitive materials, etc. by imparting higher addition value and better characteristics, particularly light resistance, solvent resistance, water resistance, chemical resistance, etc. in comparison with the prior art. As a specific example thereof, an azo compound from bisamide of 2-hydroxynaphthalene-6-carboxylic acid as a raw material has already been known (e.g. Japanese Patent Kokai Publication No. Hei 7-238231).

DISCLOSURE OF THE INVENTION

The present invention provides a novel compound whose utility is more expected as a raw material for azo compound.

The present invention provides a bisamide compound obtained from 2-hydroxynaphthalene-3, 6-dicarboxylic acid as a raw material. It is expected that an azo pigment using the compound as a coupler shows excellent chemical resistance, water resistance and solvent resistance.

Namely, the present invention relates to a bis (aminocarbonylnaphthol) derivative represented by the general formula [I], [II] or [III]:

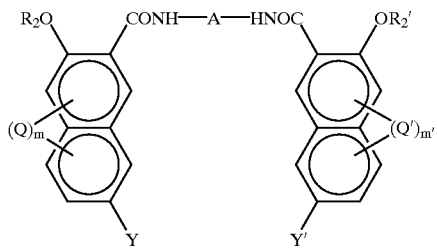

[I]

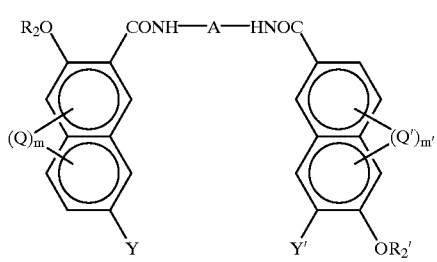

[II]

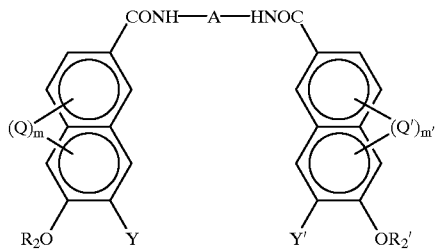

[III]

[wherein Y represents —(CONH)n—X or —COR;

Y' represents —(CONH)n—X' or —COR';

X and X' may be the same or different and represent an optionally substituted aromatic group or an optionally substituted heterocyclic group having a conjugated double bond;

n represents an integer of 1 or 2;

R and R' may be the same or the different and represent a hydroxyl group, an optionally branched alkoxyl group having 1 to 6 carbon atoms, a benzyloxy group, a phenoxy group or a phenacyloxy group;

$R_2$ and $R_2'$ represent a hydrogen atom, an optionally branched alkyl group having 1 to 6 carbon atoms, an optionally branched acyl group having 1 to 6 carbon atoms or a phenylalkyl group;

Q and Q' represent an optionally branched alkyl group having 1 to 6 carbon atoms, an optionally branched alkoxyl group having 1 to 6 carbon atoms, a halogen atom, a nitro group or a nitroso group;

m and m' represent an integer of 0 to 3; and

A represents an optionally branched alkylene group having 2 to 12 carbon atoms, or a cyclic group having a conjugated double bond].

The compound of the present invention is characterized in the bisamidation of one of carboxyl groups of naphthol having carboxyl groups at the 3- and 6-positions, using an aliphatic or aromatic diamine.

The present invention also relates to a process for producing a bis(aminocarbonylnaphthol)derivative represented by the general formula [I], [II] or [III]:

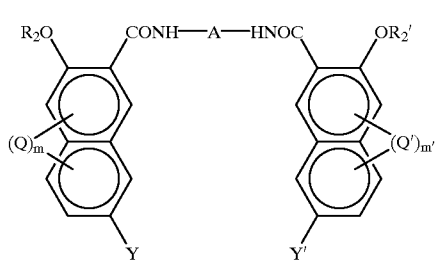

[I]

[II]

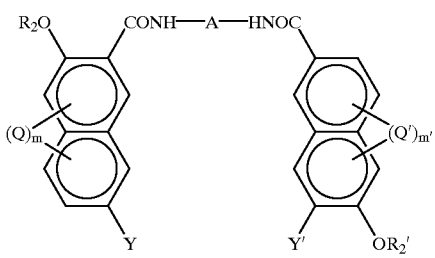

[III]

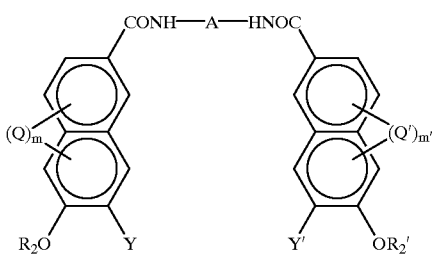

[wherein Y, Y', $R_2$, $R_2'$, Q, Q', m, m' and A are as defined above], which comprises reacting compounds represented by the general formulas [VII] [VII'] and/or [VIII] [VIII']:

[VII]

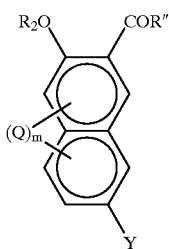

[VII']

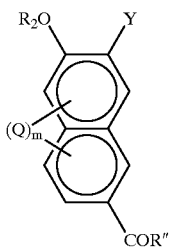

[VIII]

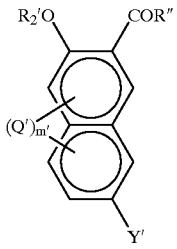

[VIII']

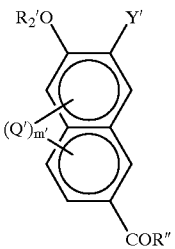

[wherein Y, Y', $R_2$, $R_2'$, Q, Q', m, and m' are as defined above; and R" represents a hydroxyl group or a halogen atom.] with diamines represented by the general formula [IX]:

$$NH_2—A—NH_2 \qquad [IX]$$

[wherein A is as defined above].

The present invention also relates to a process for producing bis(aminocarbonylnaphthol) derivative represented by the general formula [I], [II] or [III]:

[I]

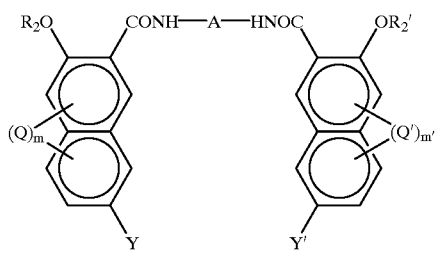

[II]

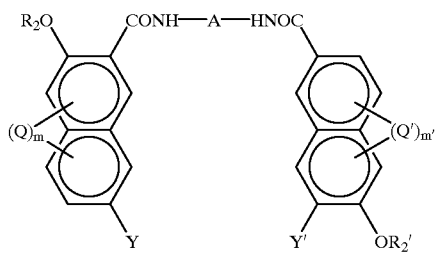

[III]

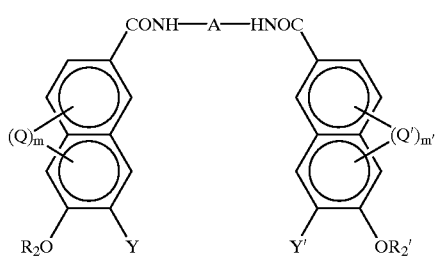

[wherein Y, Y', $R_2$, $R_2'$, Q, Q', m, m' and A are as defined above], which comprises reacting a compound represented by the general formula [VII] or [VII']:

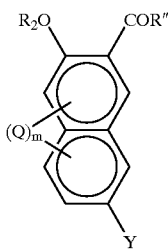

[VII]

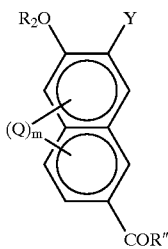

[VII']

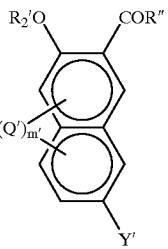

[VIII]

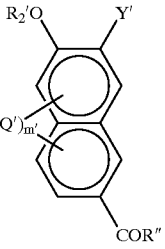

[VIII']

[wherein Y', $R_2'$, Q' and m' are as defined above; and R" represents a hydroxyl group or a halogen atom].

The compound constituting a group X or X' in Y and Y' includes optionally substituted aromatic group, such as phenyl group, naphthyl group, anthraquinonyl group, etc.; or optionally substituted heterocyclic group having a conjugated double bond, such as benzimidazolonyl group, carbazoryl group, pyridyl group, thiazolyl group, benzothiazolyl group, imidazolyl group, indolyl group, thionyl group, phenothiazinyl group, acridinyl group, quinolinyl group, etc.

The substituent of these group includes halogen, nitro group, lower alkyl group, lower alkoxy group, cyano group, phenoxy group and amide group (e.g. phenylaminocarbonyl group, etc.). Furthermore, these phenoxy group and amide group may have another substituent such as halogen, lower alkyl, lower alkoxy, alkylaminosulfonyl, nitrile, etc.

Y and Y' may represent COR or COR'. R and R' may be the same or different and represent a hydroxyl group, an optionally branched alkoxy group having 1 to 6 carbon atoms, preferably 1 to 4 carbon atoms, particularly methoxy group, ethoxy group; benzyloxy group, phenoxy group or phenacyloxy group, but the aromatic ring included in these groups may have a substituent.

Preferably, Y and Y' are respectively —CONH—X or —CONH—X'.

Groups $R_2$ and $R_2'$ may be the same or different and represent a hydrogen atom, an optionally branched alkyl group having 1 to 6 carbon atoms, preferably 1 to 4 carbon atoms, preferably methyl group, ethyl group; an acyl group having 1 to 6 carbon atoms, preferably 1 to 4 carbon atoms, particularly acetyl group; or a phenylalkyl group. The phenylalkyl group may have a substituent, for example, halogen atom, lower alkyl group, etc., and the number of carbon atoms of the alkyl group is preferably 1 to 6.

Two naphthalene nucleus of the compound represented by the general formula [I], [II] or [III] may have Q or Q', respectively, as a substituent, and examples of Q or Q' include optionally branched alkyl group having 1 to 6 carbon atoms (preferably 1 to 4 carbon atoms), optionally branched alkoxyl group having 1 to 6 carbon atoms (preferably 1 to 4 carbon atoms), halogen atom, nitro group, nitroso group, etc. The number of substituents m and m' is usually 0, but may be up to 3. When the azo compound of the present invention is used as a coupler, it should have no substituent at the 1-position of the naphthol.

[wherein Y, $R_2$, Q and m are as defined above; and R" represents a hydroxyl group or a halogen atom] with nitroamines represented by the general formula [X]:

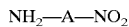

$NH_2—A—NO_2$     [X]

[wherein A is as defined above], converting the nitro group of the obtained compounds to an amino group to give an amine derivative represented by the general formula [XI] or [XI']:

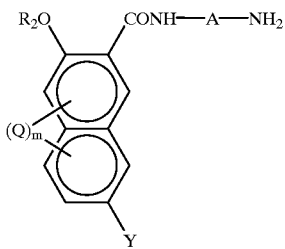

[XI]

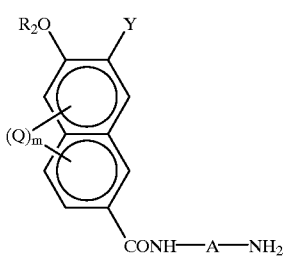

[XI']

[wherein Y, $R_2$, Q and m are as defined above], and then reacting it with the compounds represented by the general formula [VIII] or [VIII']:

A is an optionally branched alkylene group having 2 to 12 carbon atoms or a cyclic group having a conjugated double bond. As an alkylene group, those having straight-chain are preferable and those having 2 to 6 carbon atoms are particularly preferable. As the cyclic group having a conjugated double bond, an arylene group and a group having a basic skeleton represented by the general formulas [IV] and [VI] are preferred.

—Ar—M—Ar'— [IV]

[wherein Ar and Ar' independently represent an optionally substituted aryl group or a heterocyclic group having a conjugated double bond; and M represents a group chosen from the group consisting of single bond, —CH$_2$—, —CH=C(E)— (E represents a hydrogen atom, a halogen atom, a lower alkyl group or a cyano group, etc.), —O—, —S—S—S—, —CO—, —COO—, —SO$_2$—, —N(T)— (T represents an optionally substituted phenyl group or a lower alkyl group), —N=N—, —CH=CH—φ—CH=CH— (φ is an arylene group) and groups represented by the formulas [V]:

[V]

(wherein G represents —O—, —S— or —NH—)],

[VI]

[wherein L represents >N—CH$_3$, >C=O or >C=S].

Specific examples of A are as follows:

(1) an arylene group such as optionally substituted phenylene, naphthylene, anthrylene, etc.;

(2) —Ar—M—Ar'— group, for example, those wherein M is a single bond include:

those wherein M is —CH$_2$— include:

those wherein M is —CH=C(E) include:

those wherein M is —O—, —S—, —S—S—, —COO—, —SO$_2$—, —N(T)— or —N=N— include:

-continued

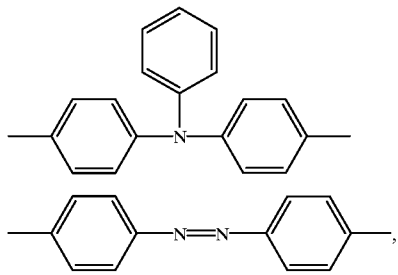

those wherein M is —CH=CH—φ—CH=CH— include:

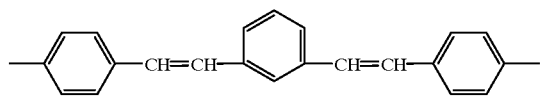

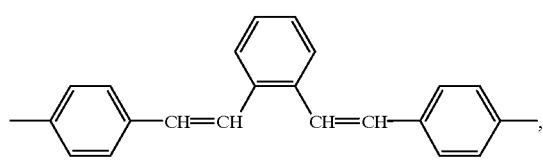

compounds wherein M is represented by the formula [V] include:

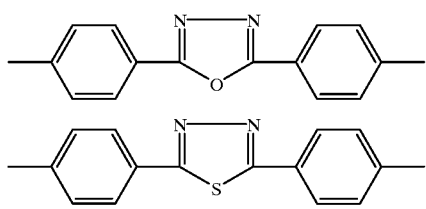

and (3) the groups having a basic skeleton wherein A is represented by the general formula [VI] include:

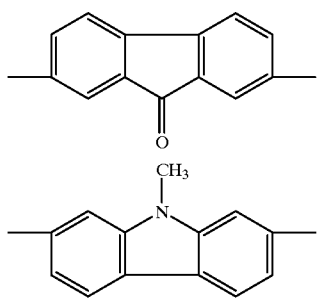

Among the compounds of the present invention, the compound represented by the general formula [I] can be obtained by reacting the compounds represented by the general formula [VII] and/or [VIII]:

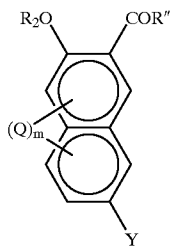

[VII]

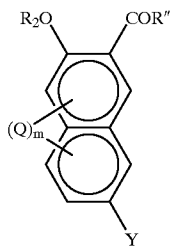

[VIII]

[wherein Y, Y', $R_2$, $R_2'$, Q, Q', m and m' are defined as above; and R" represents a hydroxyl group or a halogen atom] with aliphatic or aromatic diamines represented by the general formula [IX]:

$$NH_2—A—NH_2 \qquad [IX]$$

[wherein A is defined as above].

Among the compound represented by the general formula [VII] or [VIII], the compound wherein R" is a halogen atom can be obtained by protecting the carboxyl group at the 6-position of 2-hydroxynaphthalene-3,6-dicarboxylic acid by esterification or amidation,etc., converting the carboxyl group at the 3-position into an acid chloride using thionyl chloride or cyanuric chloride,etc. and then reacting the resultant compound with an aromatic diamine. On the other hand, the compound wherein R" is a hydroxyl group can be obtained by protecting a carboxyl group at the 6-position by esterification or amidation,etc. and then reacting the resultant compound with an aromatic diamine in the presence of phosphorous trichloride and sulfolane. If necessary, the ester at the 6-position may be hydrolyzed, thereby introduced a desired group according to the normal method.

Regarding the compound represented by the general formula [II], as shown in the scheme:

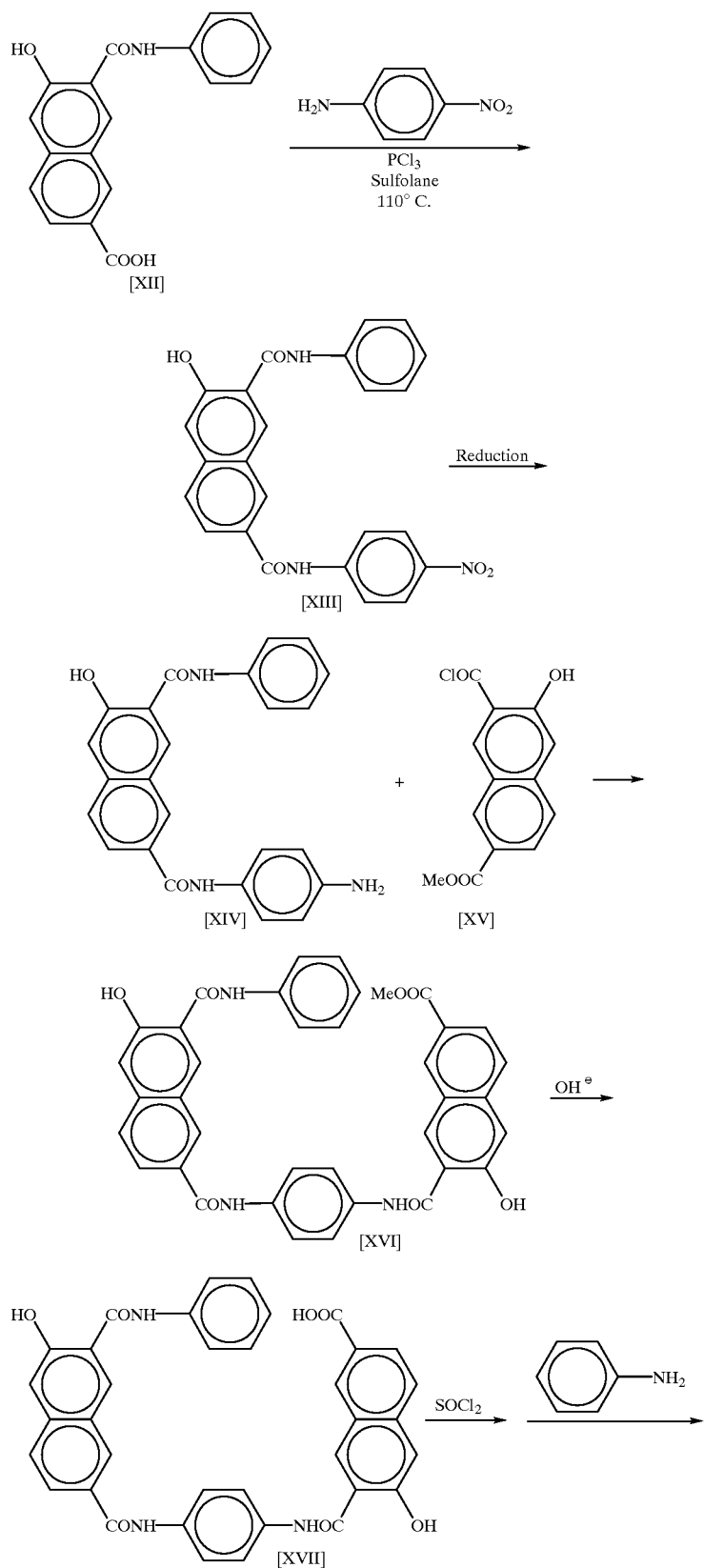

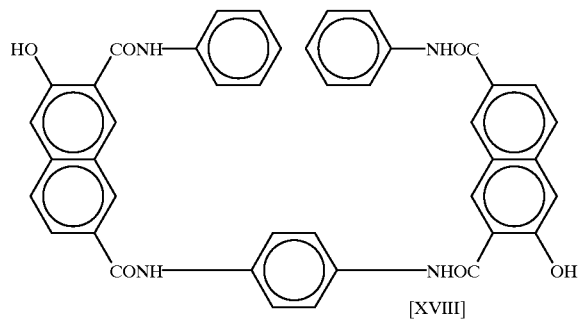

[XVIII]

[wherein Me represents a protecting group such as methyl group]

the objective compound [XVIII] (namely, compound corresponding to the general formula [11]) can be obtained by reacting a 3-amide compound [XII] with an aromatic amine having a nitro group in the presence of phosphorous trichloride and sulfolane, thereby amidating a carboxyl group at the 6-position to obtain the compound having a nitro group [XIII], reducing the nitro group of the compound into an amino group according to the normal method to obtain a compound [XIV], reacting the compound [XIV] with 2-hydroxynaphthalene-3, 6-dicarboxylic acid [XV] obtained by protecting a carboxyl group at the 6-position and converting a carboxyl group at the 3-position into an acid chloride to obtain a 3, 6-diamide compound [XVI], optionally removing a protecting group from a carboxyl group derived from the dicarboxylic acid [XV], optionally converting into an acid chloride using thionyl chloride and then reacting the acid chloride with desired amines.

Furthermore, as shown in the following scheme:

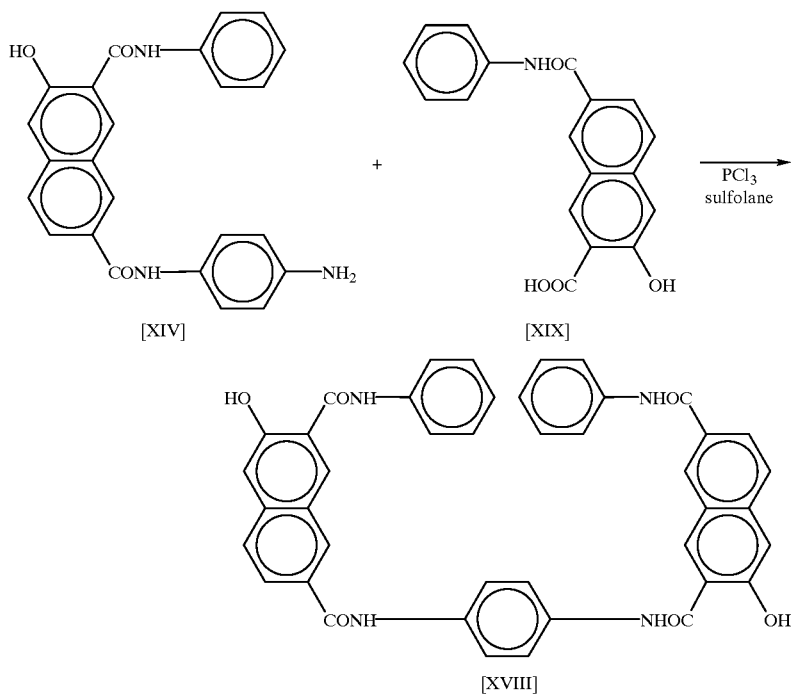

the objective compound [XVIII] can be also obtained by directly reacting the compound [XIV] with 2-hydroxynaphthalene-3,6-dicarboxylic acid [XIX] obtained by amidating the carboxyl group at the 6-position using a desired amine in the presence of phosphorous trichloride and sulfolane.

Among the compound represented by the general formula [VII'] or [VIII'], the compound wherein R" is a halogen atom can be obtained by protecting the carboxylic group at the 3-position of 2-hydroxynaphthalene-3, 6-dicarboxylic acid as a raw material by esterification or amidation,etc. converting the carboxyl group at the 6-position into an acid chloride using thionyl chloride or cyanuric chloride,etc. and then reacting the acid chloride with an aromatic diamine. If necessary, the ester at the 3-position may be hydrolyzed, thereby introduced a desired group according to the normal method. On the other hand, the compound wherein R" is a hydroxyl group can be obtained by protecting the carboxyl group at the 3-position by esterification or amidation, etc. and then reacting the resultant compound with an aromatic diamine in the presence of phosphorous trichloride and sulfolane. The example of protecting the carboxyl group at the 3-position and then reacting the carboxyl group at the 6-position with an aromatic diamine is shown below.

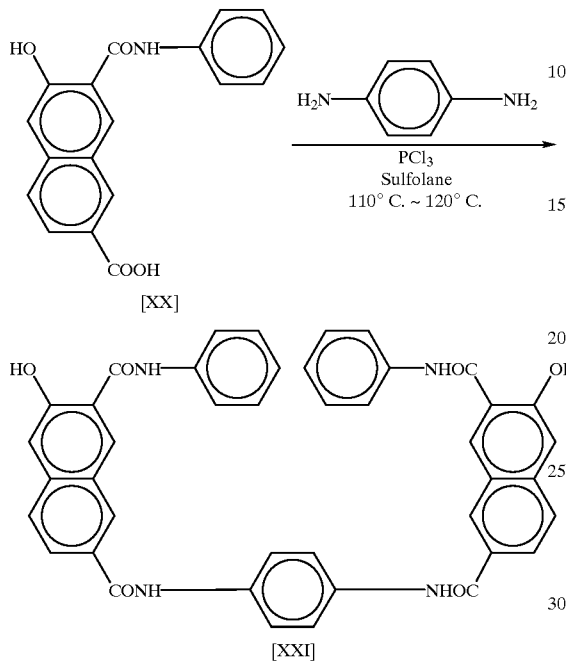

The compound of the present invention is extremely useful as a coupler of a diazo compound and a raw material of an azo pigment.

The following Examples further illustrate the method for purification from a mixture.

EXAMPLE 1

1,4-bis(2'-hydroxy-6'-hydroxycarbonyl-naphth-3'-ylcarbonylamino)phenylene

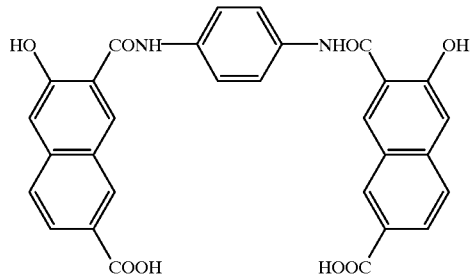

To a suspension of 394 g of xylene, 0.08 g of N,N-dimethylformamide and 22.2 g of 2-hydroxy-3-hydroxycarbonyl-6-methoxycarbonylnaphthalene, 54.3 g of thionyl chloride was added and the mixture was reacted at 70° C. for 15 hours.

Then, the reaction solution was concentrated and excess thionyl chloride was distilled off to obtain a xylene solution of 2-hydroxy-3-chlorocarbonyl-6-methoxycarbonylnaphthalene.

To this solution, 150 g of N-methyl-2-pyrrolidone solution dissolving 3.3 g of p-phenylenediamine was added, and the mixture was reacted at 70 to 80° C. for 17 hours.

Then, xylene was recovered and water was added to the residue solution to deposit a crystal. After filtrating and washing with water, the resulting crystal was further reflux-washed with 600 g of methanol for 1 hour. After cooling, the crystal was filtrated to obtain 15.1 g of a powder of 1,4-bis (2'-hydroxy-6'-methoxycarbonyl-naphth-3'-ylcarbonylamino) phenylene.

This powder was added to a solution of 540 g of 10% NaOH and 360 g of methanol and, after the reflux reaction was performed for 6 hours, methanol was recover and 10% HCl was added to the residue solution to deposit the crystal.

This crystal was filtrated, washed with water and then dried to obtain 5.0 g of a powder of 1,4-bis (2'-hydroxy-6'-hydroxycarbonyl-naphth-3'-ylcarbonylamino) phenylene.

Melting point/decomposition point: 369.7° C.

An infrared absorption spectrum (KBr tablet method) is shown in FIG. 1.

EXAMPLE 2

1,4-bis (2'-hydroxy-6'-phenylaminocarbonyl-naphth-3'-ylcarbonylamino) phenylene

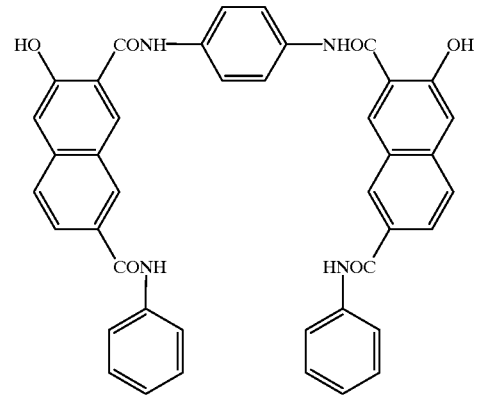

To a suspension of 394 g of xylene, 0.08 g of N,N-dimethylformamide and 23.3 g of 2-hydroxy-3-hydroxycarbonyl-6-phenylaminocarbonylnaphthalene, 54.3 g of thionyl chloride was added and the mixture was reacted at 70° C. for 15 hours.

Then, the reaction solution was concentrated and excess thionyl chloride was distilled off to obtain a xylene solution of 2-hydroxy-3-chlorocarbonyl-6-phenylaminocarbonylnaphthalene.

To this solution, 150 g of N-methyl-2-pyrrolidone solution dissolving 3.3 g of p-phenylenediamine was added and the mixture was reacted at 70 to 80° C. for 17 hours.

Then, xylene was recovered and water was added to the residue solution to deposit a crystal. After filtrating and washing with water, the resulting crystal was further reflux-washed with 600 g of methanol for 1 hour. After cooling, the crystal was filtrated and dried to obtain 6.4 g of a powder of 1,4-bis (2'-hydroxy-6'-phenylaminocarbonyl-naphth-3'-ylcarbonylamino) phenylene.

Melting point/decomposition point: 358.8° C.

An infrared absorption spectrum (KBr tablet method) is shown in FIG. 2.

EXAMPLE 3

1,4-bis [2'-hydroxy-6'- (3''-methylphenylaminocarbonyl) -naphth-3'-ylcarbonylamino] phenylenel

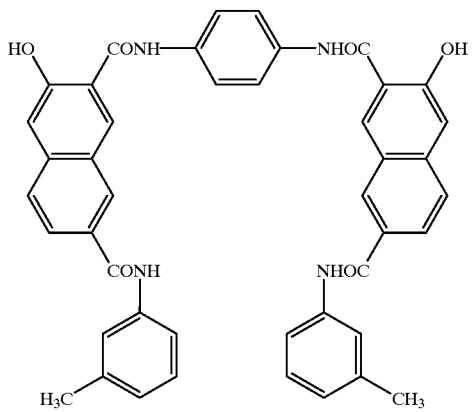

According to the same manner as described in Example 2 except for replacing 2-hydroxy-3-hydroxycarbonyl-6-phenylaminocarbonylnaphthalene used in Example 2 by 24.4 g of 2-hydroxy-3-hydroxycarbonyl-6-(3'-methylphenylaminocarbonyl) naphthalene, 7.5 g of a powder of 1,4-bis [2'-hydroxy-6'-(3'-methylphenylaminocarbonyl) -naphth-3'-ylcarbonylamino] phenylene was obtained.

Melting point/decomposition point: 417.5° C.

An infrared absorption spectrum (KBr tablet method) is shown in FIG. 3.

FD-MS(mass spectrum by a field desorption ionization mass spectrometry) is shown in FIG. 4.

m/z 714

EXAMPLE 4

1,4-bis (2'-hydroxy-3'-phenylaminocarbonyl-naphth-6'-ylcarbonylamino) phenylene

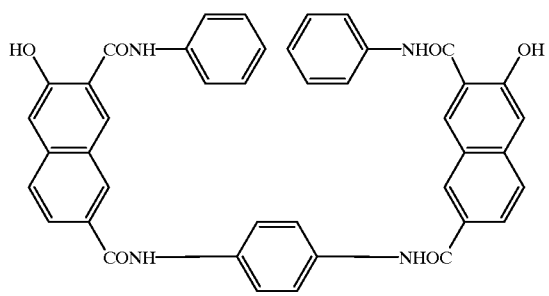

To a suspension of 25 g of sulfolane, 0.59 g (5.4 mmol) of p-phenylenediamine and 4.0 g of 2-hydroxy-3-phenylaminocarbonyl-6-hydroxycarbonylnaphthalene, 1.4 g of phosphorous trichloride was added and the mixture was reacted at 120° C. for 23 hours.

After cooling, the crystal was filtered by means of suction to obtain 14 g of a pale yellow powdered crystal (undried product). After the powdered crystal was dissolved in 50 g of N-methyl-2-pyrrolidone, the solution was filtered with 0.5 g of activated carbon. Then, 60 g of methanol was added to deposit a crystal. The deposited crystal was filtered, washed with water and methanol, and then dried to obtain 1.24 g of a pale yellow powdered crystal of the title product.

Melting point/decomposition point: 432.9° C.

An infrared absorption spectrum (KBr tablet method) is shown in FIG. 5.

FD-MS (mass spectrum by a field desorption ionization mass spectrometry) is shown in FIG. 6.

m/z 686

EXAMPLE 5

Synthesis of 1- (2'-hydroxy-3'-phenylaminocarbonyl-naphth-6'-yl-carbonylamino) -4- (2'-hydroxy-6'-phenylaminocarbonyl-naphth-3'-yl-carbonylamino) phenylene

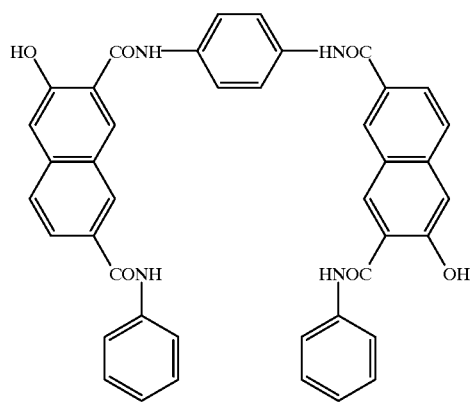

According to the method as described in Example 2, a xylene solution of 2-hydroxy-3-chlorocarbonyl-6-phenylaminocarbonylnaphthalene was obtained. Then, this solution was added dropwise at 75° C. to a solution obtained previously by dissolving 6.0 g of 2-hydroxy-3-phenylaminocarbonyl-6- (4'-aminophenyl) aminocarbonyl-naphthalene into 50 g of N-methyl-2-pyrrolidone and 100 g of xylene. After reacting for about 15 hours, 300 g of water and 100 g of methanol were added to the solution and the deposited crystal was recovered by filtration. Then, the crystal was purified according to the method described in Example 2 to obtain 4.9 g of a powder of the titled product.

Melting point/decomposition point: 390.4° C.

An infrared absorption spectrum (KBr tablet method) is shown in FIG. 7.

EXAMPLE 6

Synthesis of 1-(2'-hydroxy-3'-phenylaminocarbonyl-naphth-6'-yl-carbonylamino)-3-(2'-hydroxy-6'-phenylaminocarbonyl-naphth-3'-yl-carbonylamino) phenylene

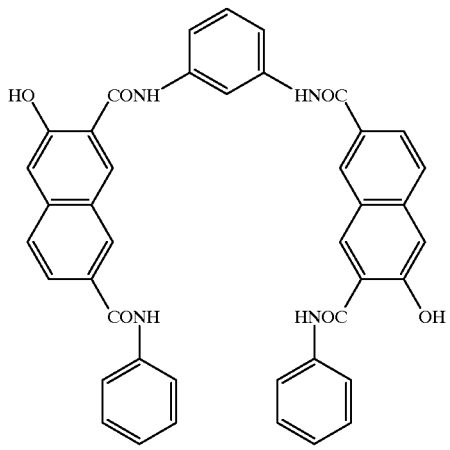

According to the same manner as described in Example 5 except for replacing 2-hydroxy-3-phenylaminocarbonyl-6-(4'-aminophenyl) aminocarbonylnaphthalene of Example 5 by 2-hydroxy-3-phenylaminocarbonyl-6-(3'-aminophenyl) aminocarbonylnaphthalene, 5.2 g of a powder of the titled product was obtained.

Melting point/decomposition point: 334.1° C.

An infrared absorption spectrum (KBr tablet method) is shown in FIG. 8.

EXAMPLE 7

Synthesis of bis {4-(2'-hydroxy-6'-phenylaminocarbonyl-naphth-3'-yl-carbonylamino) phenyl} methane According to the same manner as described in Example 2 except for replacing p-phenylenediamine of Example 2 by 1.32 g of 4,4'-diaminodiphenylmethane, 1.87 g of a powder of the titled product was obtained.

Melting point/decomposition point: 353.4° C.

An infrared absorption spectrum (KBr tablet method) is shown in FIG. 9.

EXAMPLE 8

Synthesis of bis {4-(2'-hydroxy-3'-phenylaminocarbonyl-naphth-6'-yl-carbonylamino) phenyl} methane

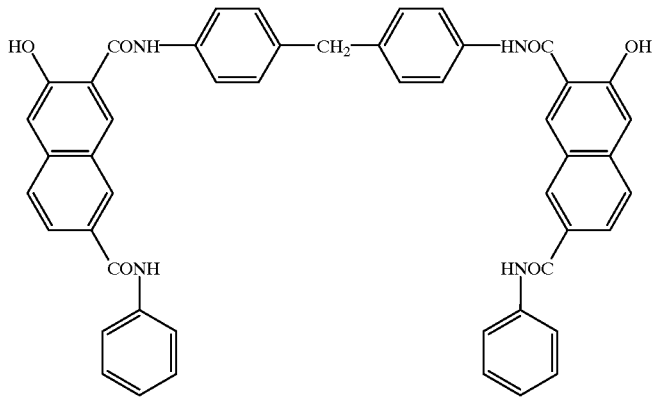

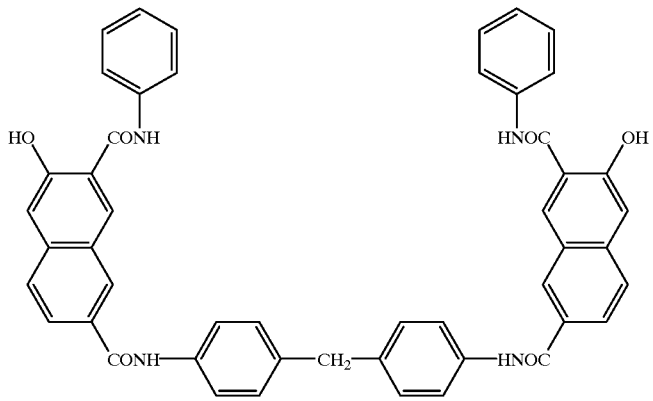

According to the same manner as described in Example 2 except for replacing 2-hydroxy-3-hydroxycarbonyl-6-phenylaminocarbonylnaphthalene of Example 2 by 2-hydroxy-6-hydroxycarbonyl-3-phenylaminocarbonylnaphthalene, and replacing p-phenylenediamine by 1.32 g of 4,4'-diaminodiphenylmethane, 1.76 g of a powder of the titled product was obtained.

Melting point/decomposition point: 368.2° C.

An infrared absorption spectrum (KBr tablet method) is shown in FIG. 10.

EXAMPLE 9

Synthesis of bis {4-(2'-hydroxy-6'-phenylaminocarbonyl-naphth-3'-yl-carbonylamino) phenyl} ether

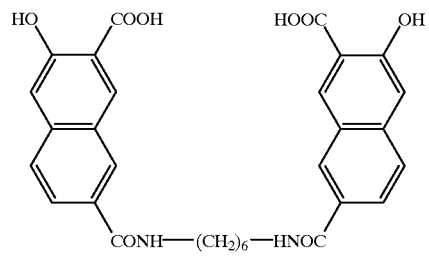

According to the same manner as described in Example 1 except for replacing p-phenylenediamine of Example 1 by 4.9 g of 1,6-hexamethylene diamine, and replacing 10%-NaOH by 7.8 g of sodium carbonate and 250 g of water, 13.7 g of a grayish white powder of 1,6-bis (2'-hydroxy-3'-hydroxycarbonyl-naphth-6'-yl-carbonylamino) hexamethylene was obtained.

Melting point/decomposition point: 320.2° C.

An infrared absorption spectrum (KBr tablet method) is shown in FIG. 12.

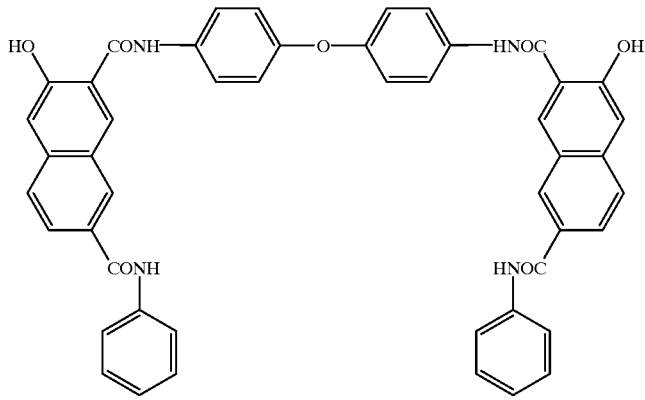

According to the same manner as described in Example 2 except for replacing p-phenylenediamine of Example 2 by 1.33 g of 4,4'-diaminodiphenyl ether, 1.84 g of a powder of the titled product was obtained.

Melting point/decomposition point: 401.3° C.

An infrared absorption spectrum (KBr tablet method) is shown in FIG. 11.

EXAMPLE 10

Synthesis of 1,6-bis (2'-hydroxy-3'-hydroxycarbonyl-naphth-6'-yl-carbonylamino) hexamethylene

EXAMPLE 11

Synthesis of 2,5-bis {4'- (2'-hydroxy-6'- (5-chloro-2,4-dimethoxyphenyl) aminocarbonyl-naphth-3'-yl-carbonylamino) phenyl}- 1,3,4-oxadiazole

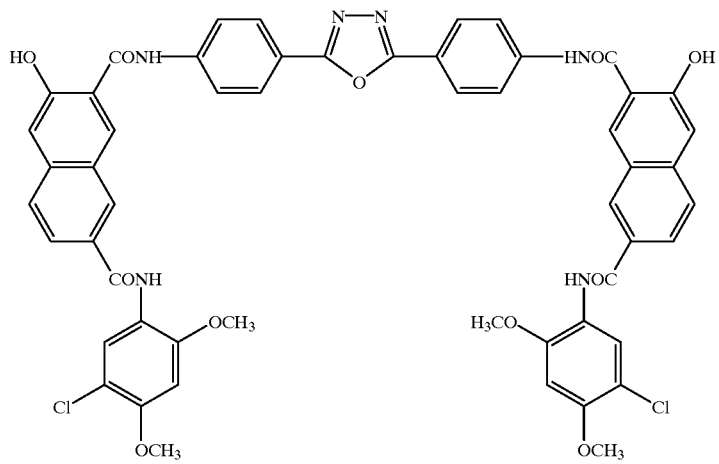

According to the same manner as described in Example 4 except for replacing p-phenylenediamine of Example 4 by 1.3 g of 2,5-bis (4'-aminophenyl) -1,3,4-oxadiazole dihydrochloride, and replacing 2-hydroxy-3-phenylaminocarbonyl-6-hydroxycarbonylnaphthalene by 3.1 g of 2-hydroxy-6-hydroxycarbonyl-3- (5'-chloro-2', 4'-dimethoxyphenyl) aminocarbonylnaphthalene, 1.7 g of a powder of the titled product was obtained.

Melting point/decomposition point: 423.5° C.

An infrared absorption spectrum (KBr tablet method) is shown in FIG. 13.

EXAMPLE 12

Synthesis of 2,7-bis {2'-hydroxy-3'- (5"-chloro-2", 4"-dimethoxyphenyl) aminocarbonyl-naphth-6'-yl-carbonylamino} -9-fluorenone According to the same manner as described in Example 4 except for replacing p-phenylenediamine of Example 4 by 1.6 g of 2, 7-diamino-9-fluorenone dihydrochloride, and replacing 2-hydroxy-3-phenylaminocarbonyl-6-hydroxycarbonylnaphthalene by 3.1 g of 2-hydroxy-6-hydroxycarbonyl-3- (5'-chloro-2', 4'-dimethoxyphenyl) aminocarbonylnaphthalene, 1.9 g of a powder of the titled product was obtained.

Melting point/decomposition point: 238.6° C.

An infrared absorption spectrum (KBr tablet method) is shown in FIG. 14.

EXAMPLE 13

Synthesis of 2,7-bis (2'-hydroxy-3'-phenylaminocarbonyl-naphth-6'-yl-carbonylamino) -9-fluorenone

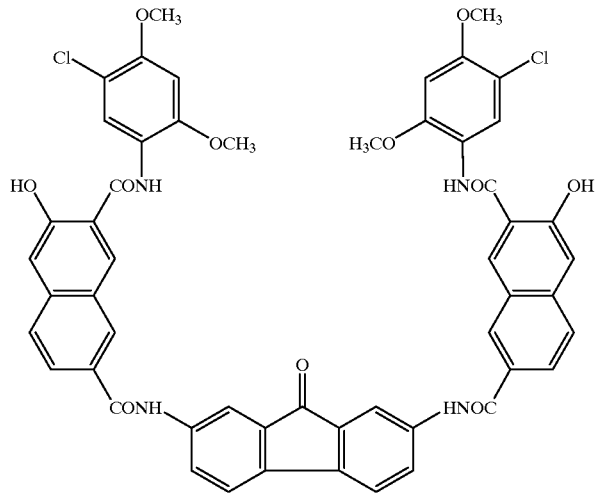

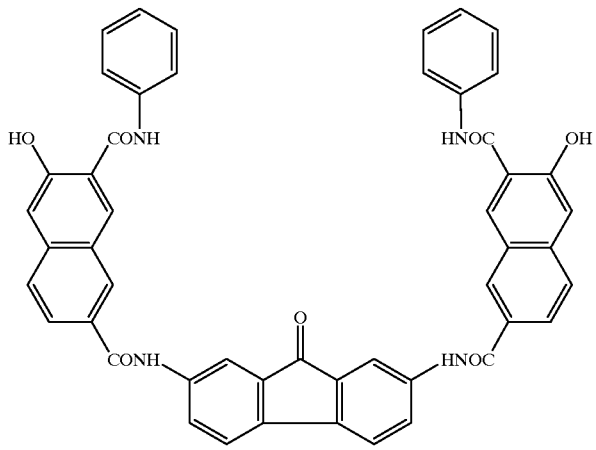

According to the same manner as described in Example 4 except for replacing p-phenylenediamine of Example 4 by 1.6 g of 2,7-diamino-9-fluorenone dihydrochloride, 1.8 g of a powder of the titled product was obtained.

Melting point/decomposition point: 250.1° C.

An infrared absorption spectrum (KBr tablet method) is shown in FIG. 15.

EXAMPLE 14

Synthesis of 1,4-bis {2'-hydroxy-6'-(benzimidazolon-5'-ylaminocarbonyl)-naphth-3'-yl-carbonylamino} phenylene

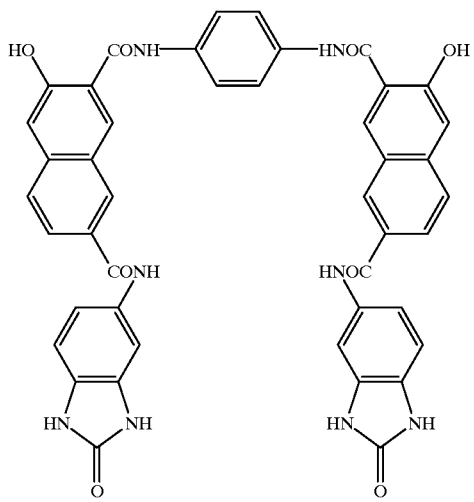

According to the same manner as described in Example 2 except for replacing 2-hydroxy-3-hydroxycarbonyl-6-phenylaminocarbonylnaphthalene of Example 2 by 2-hydroxy-3-hydroxycarbonyl-6-(benzimidazolon-5'-ylaminocarbonyl) naphthalene, 1.84 g of a powder of the titled product was obtained.

Melting point/decomposition point: 455.8° C.

An infrared absorption spectrum (KBr tablet method) is shown in FIG. 16.

INDUSTRIAL APPLICABILITY

The compound of the present invention can be used as a coupler for an azo compound.

Figure 1:
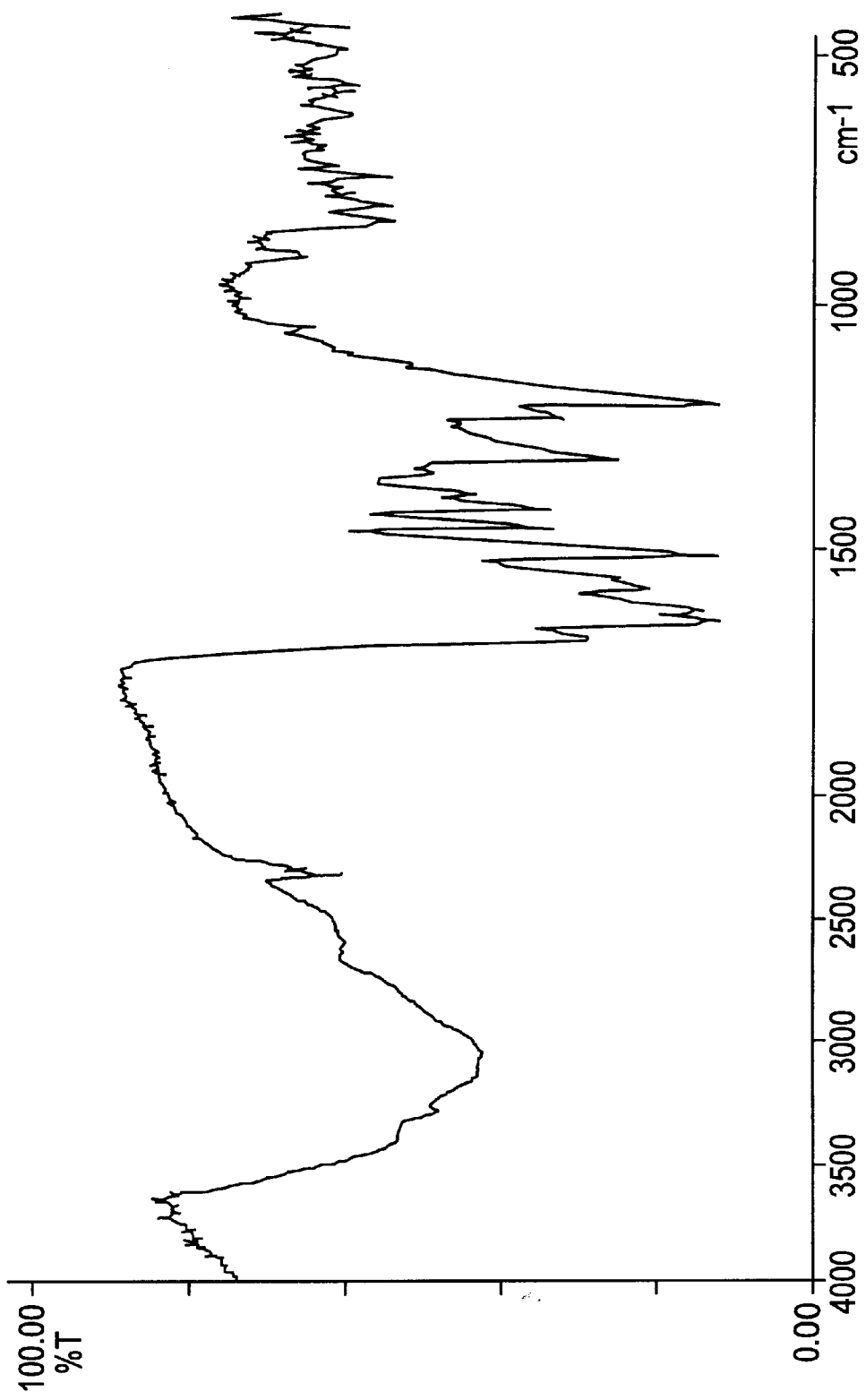
FIG. 1 is an infrared absorption spectrum of the compound obtained in Example 1.
Figure 2:
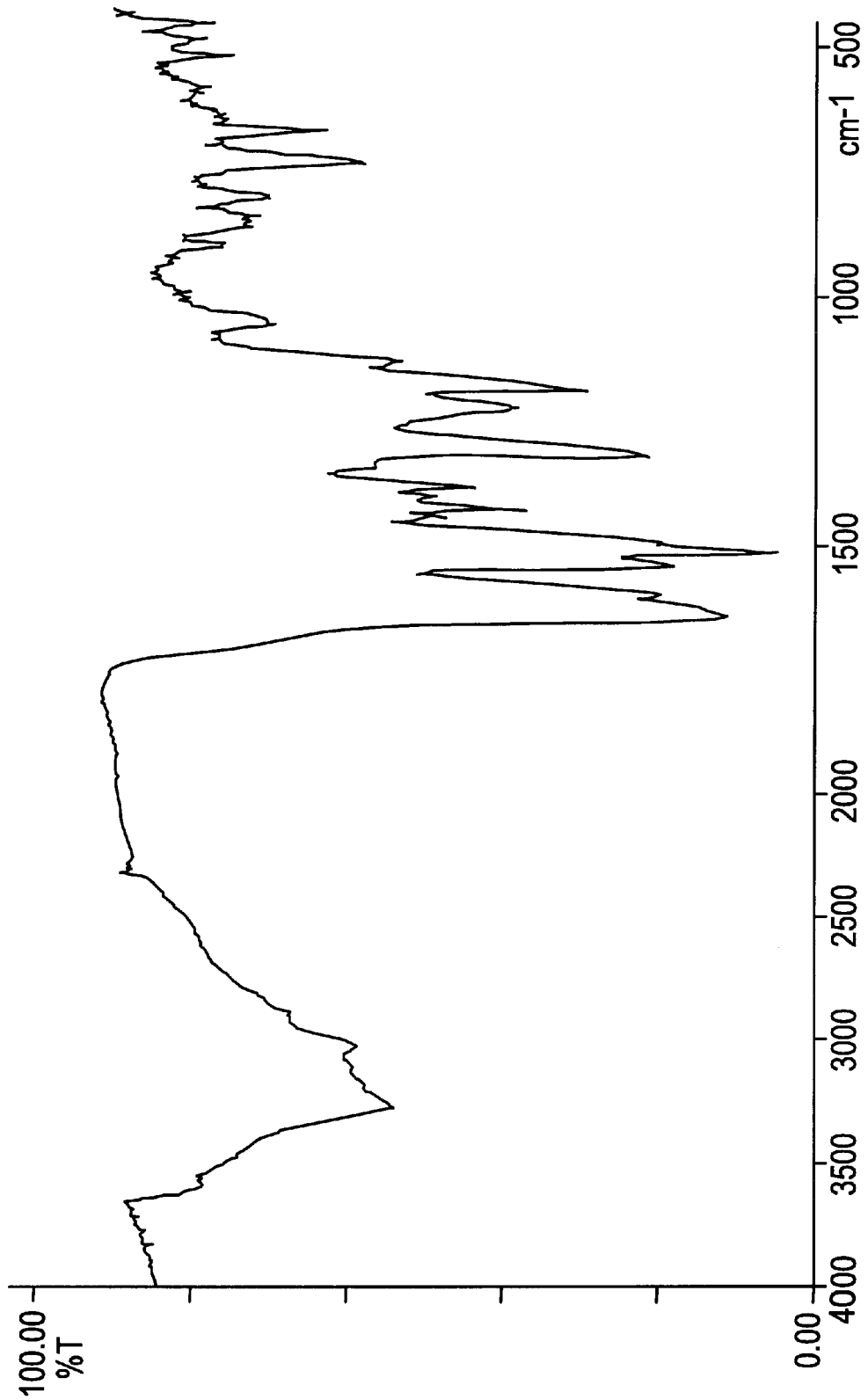
FIG. 2 is an infrared absorption spectrum of the compound obtained in Example 2.
Figure 3:
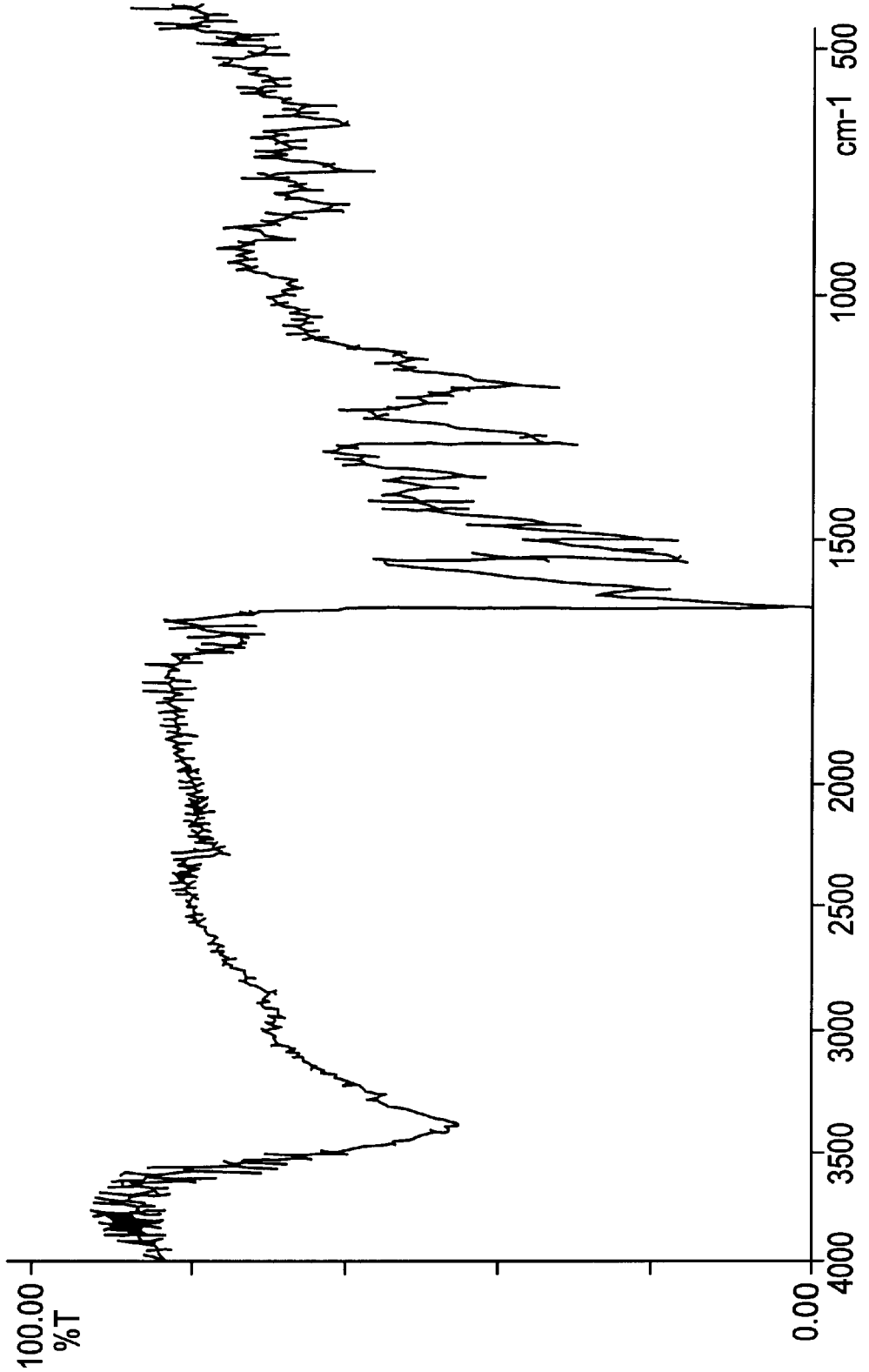
FIG. 3 is an infrared absorption spectrum of the compound obtained in Example 3.
Figure 4:
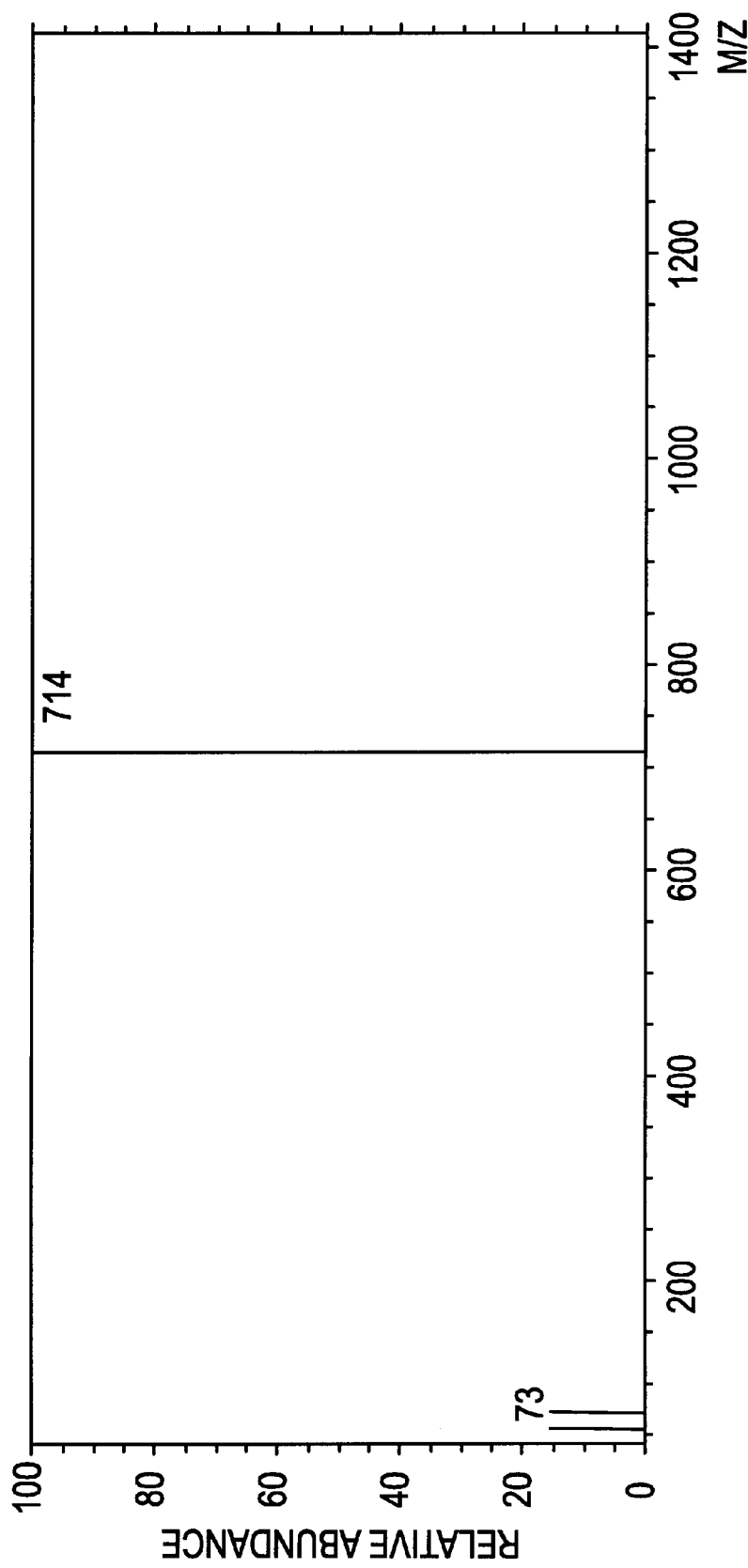
FIG. 4 is a mass spectrum by a field desorption ionization mass spectrometry of the compound obtained in Example 3.
Figure 5:
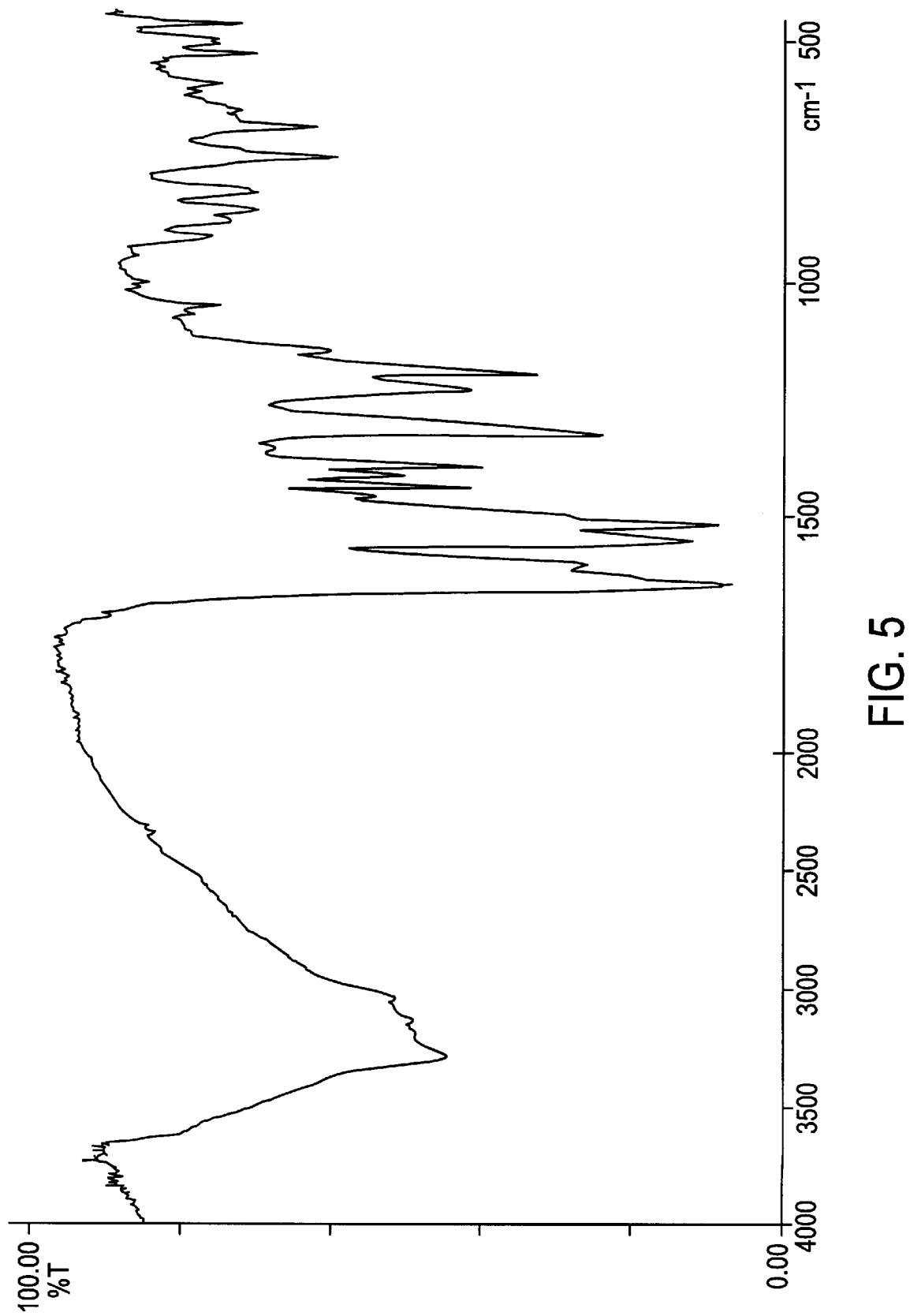
FIG. 5 is an infrared absorption spectrum of the compound obtained in Example 4.
Figure 6:
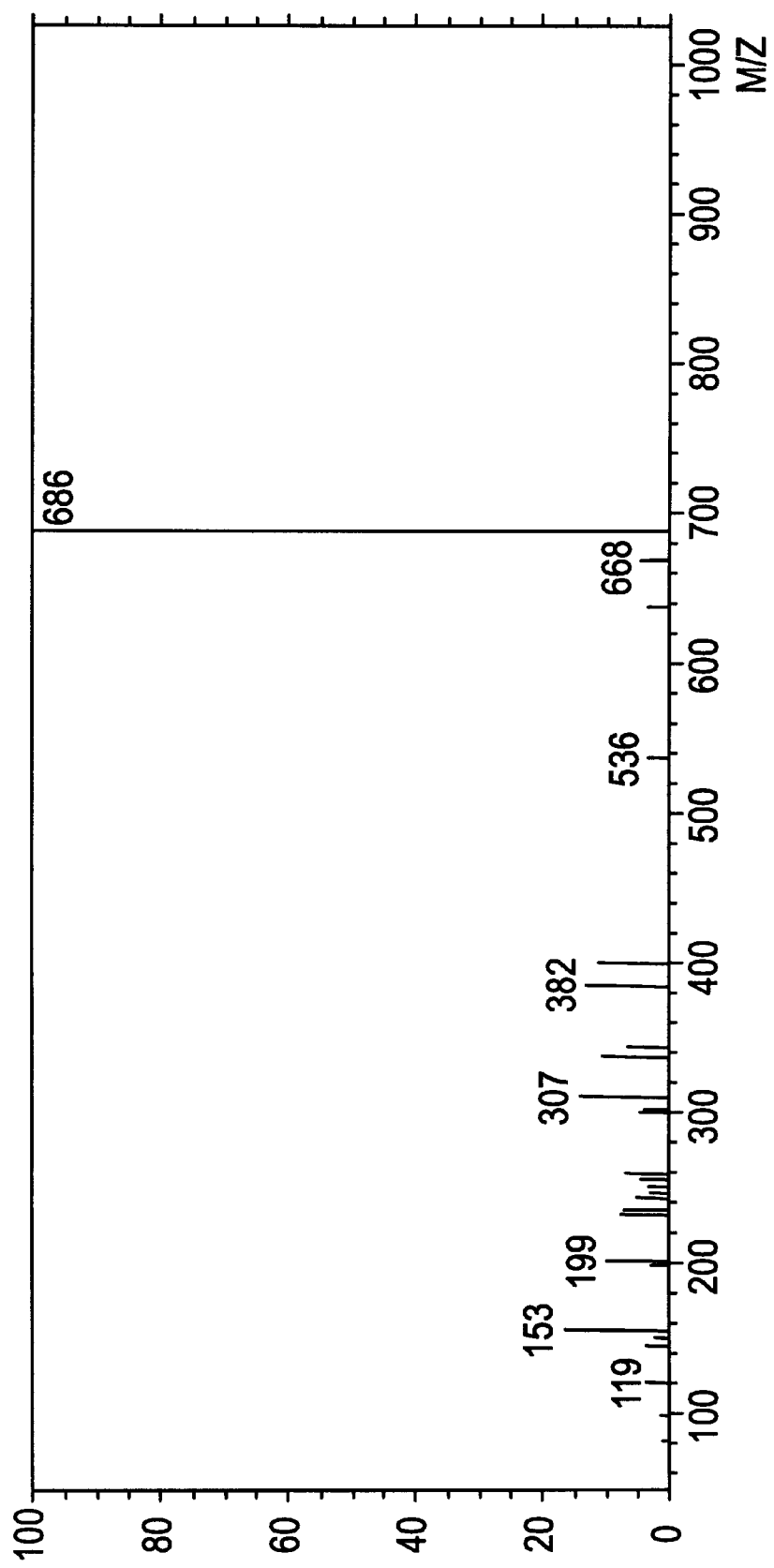
FIG. 6 is a mass spectrum by a field desorption ionization mass spectrometry of the compound obtained in Example 4.
Figure 7:
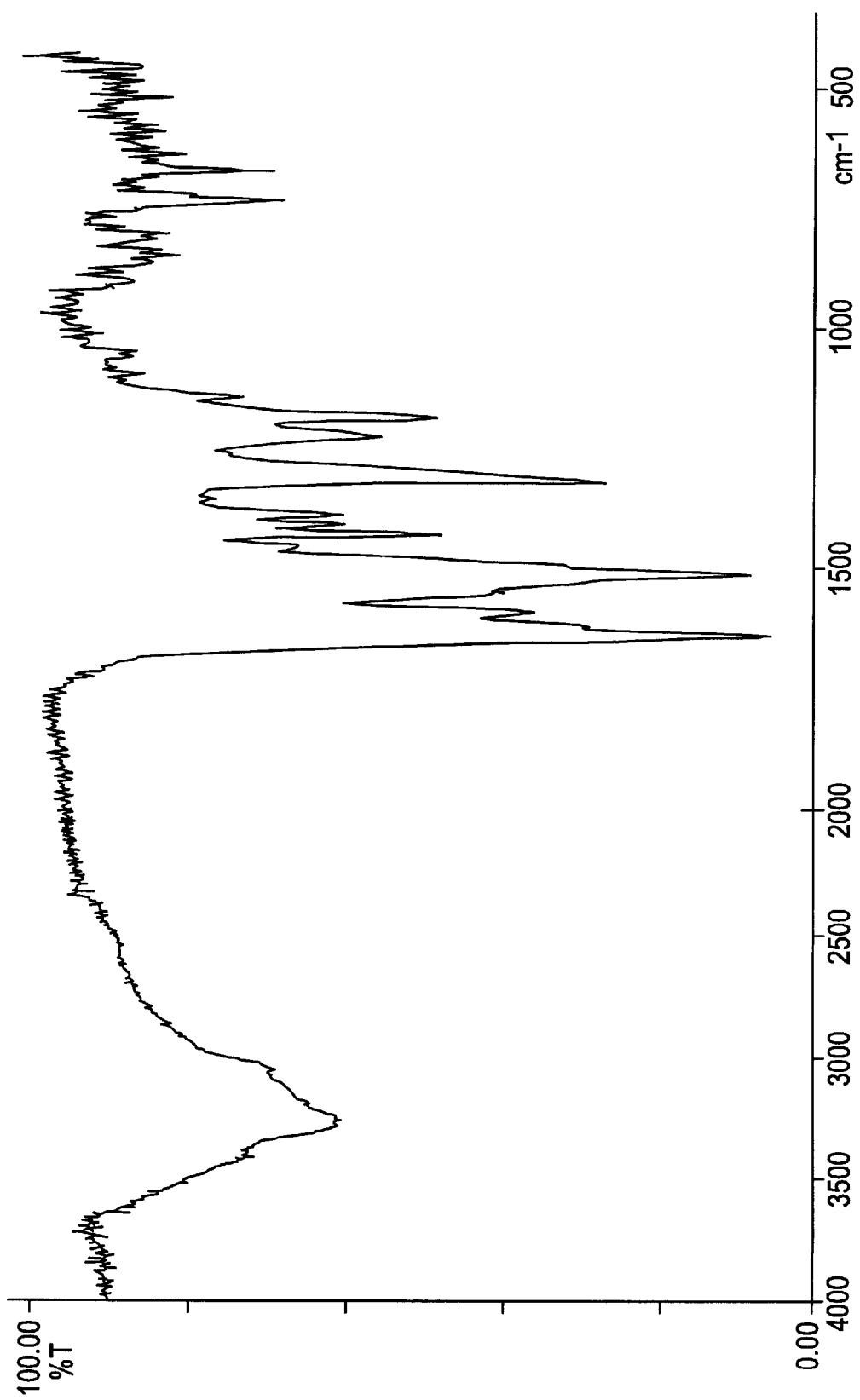
FIG. 7 is an infrared absorption spectrum of the compound obtained in Example 5.
Figure 8:
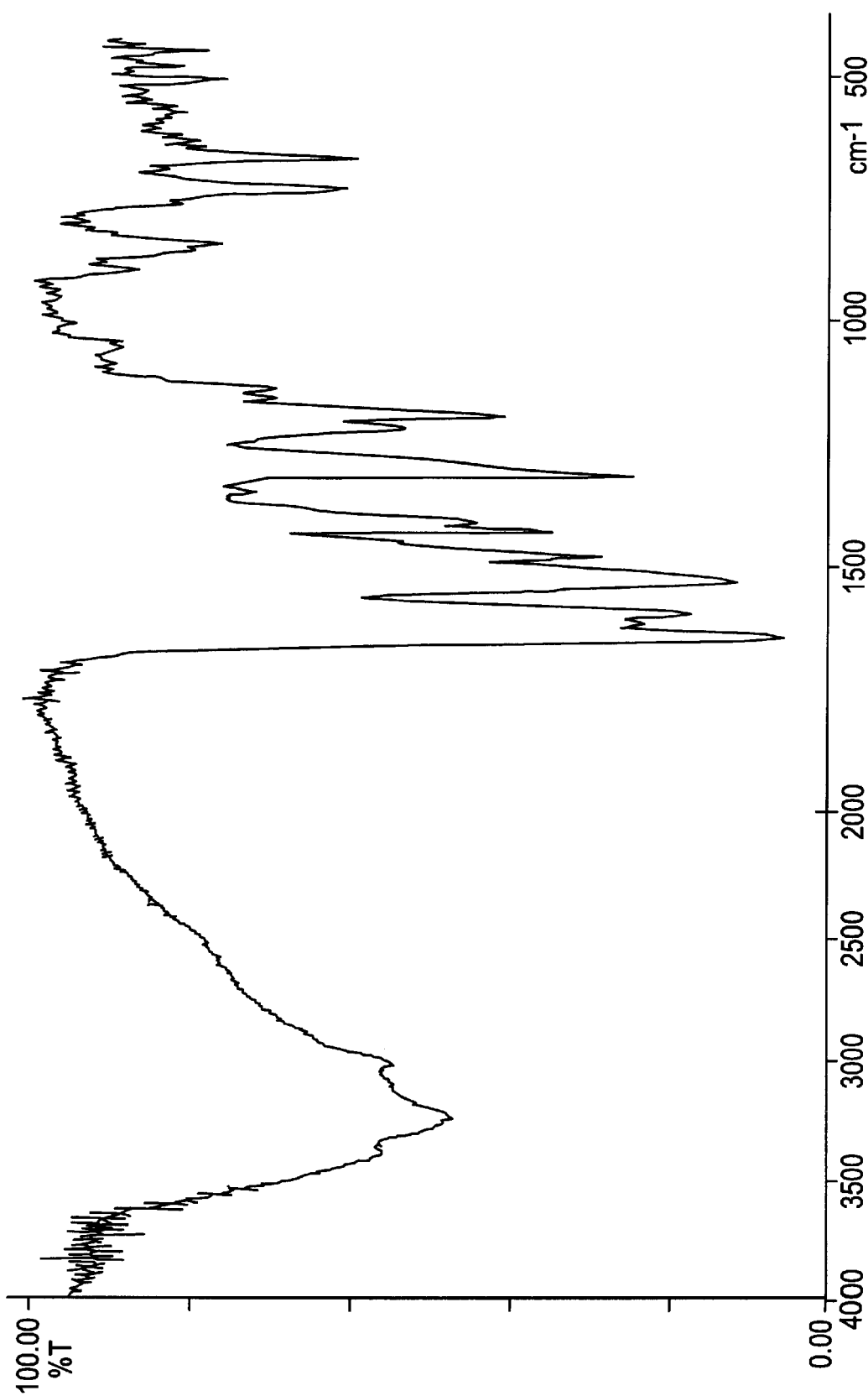
FIG. 8 is an infrared absorption spectrum of the compound obtained in Example 6.
Figure 9:
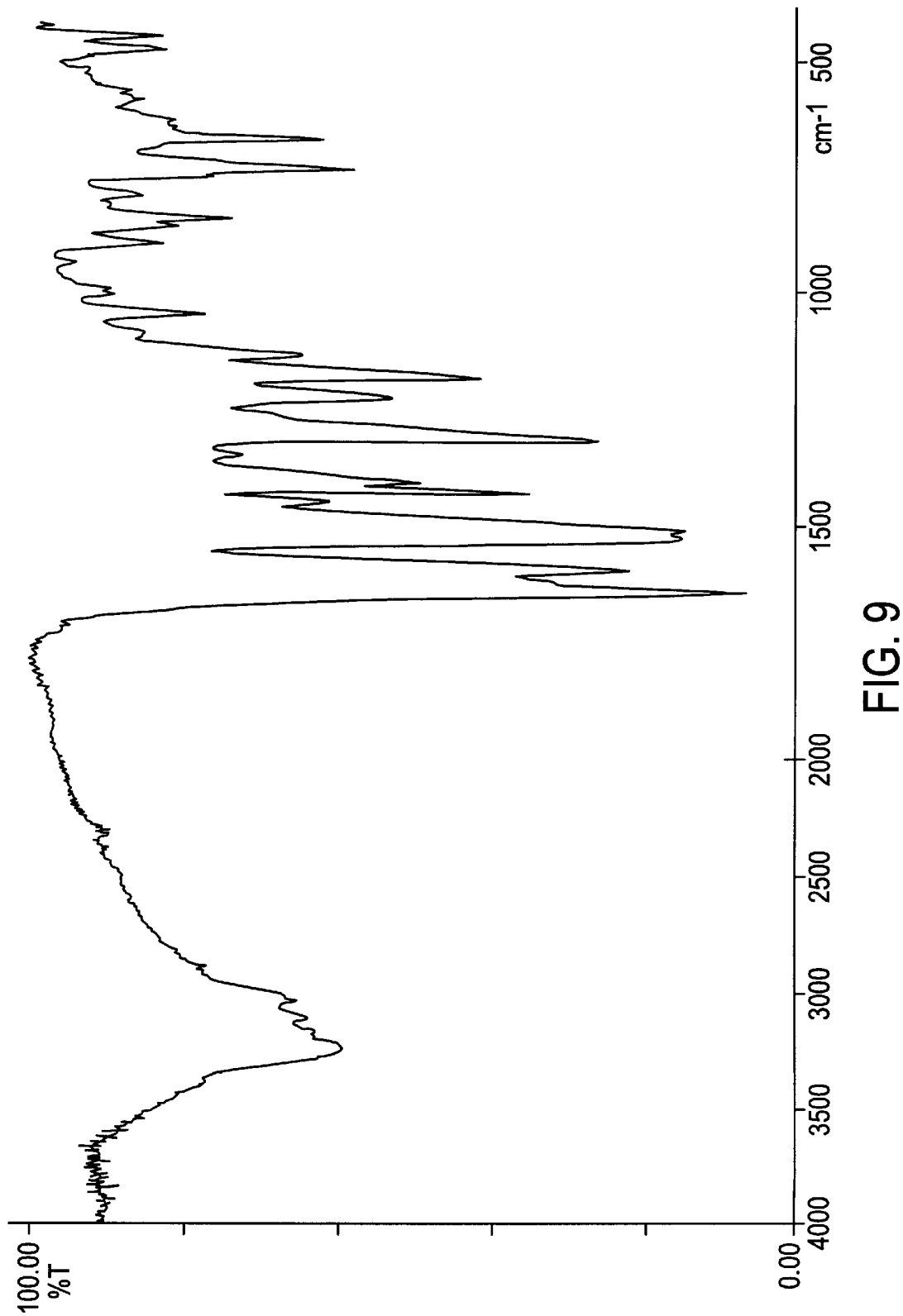
FIG. 9 is an infrared absorption spectrum of the compound obtained in Example 7.
Figure 10:
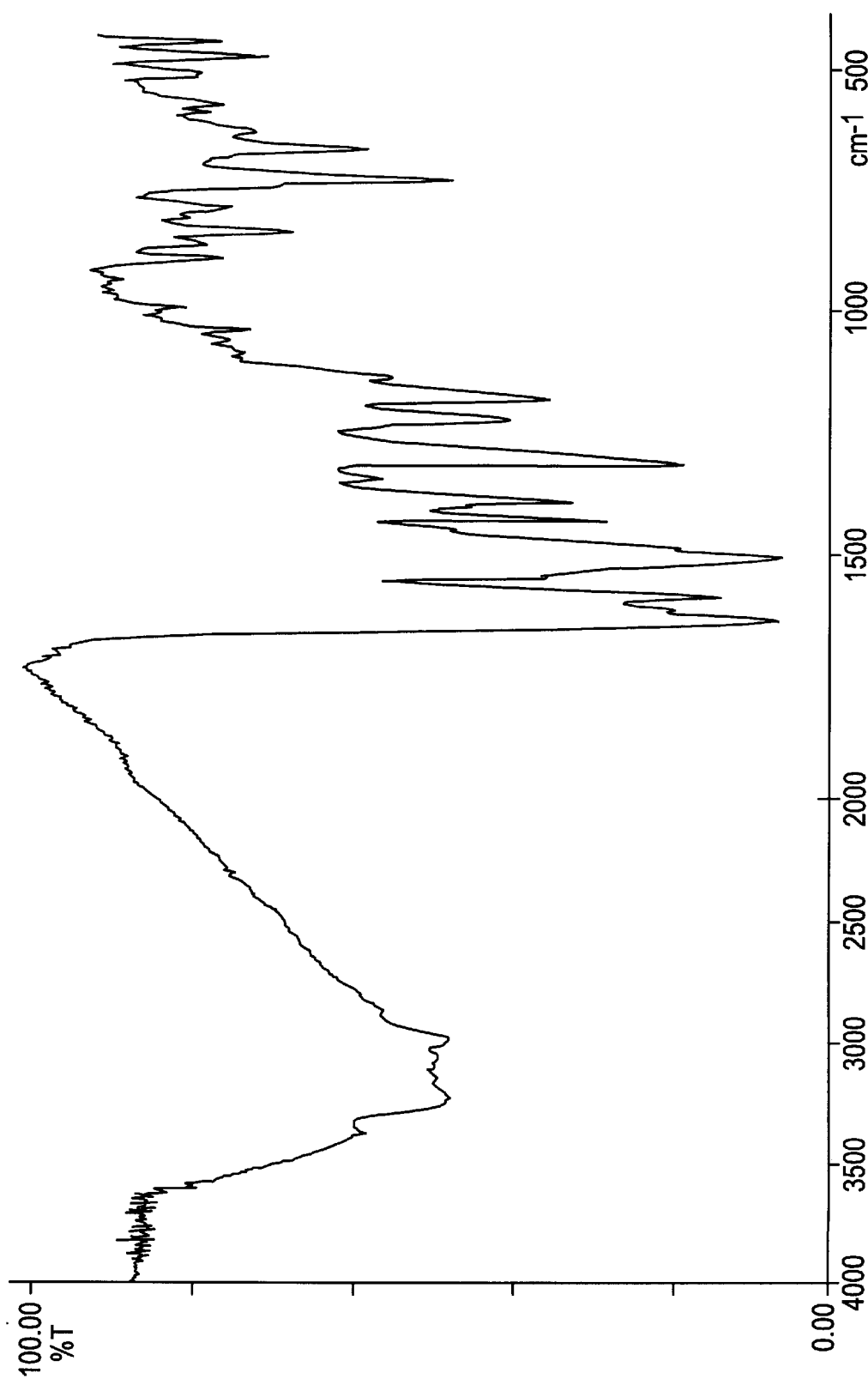
FIG. 10 is an infrared absorption spectrum of the compound obtained in Example 8.
Figure 11:
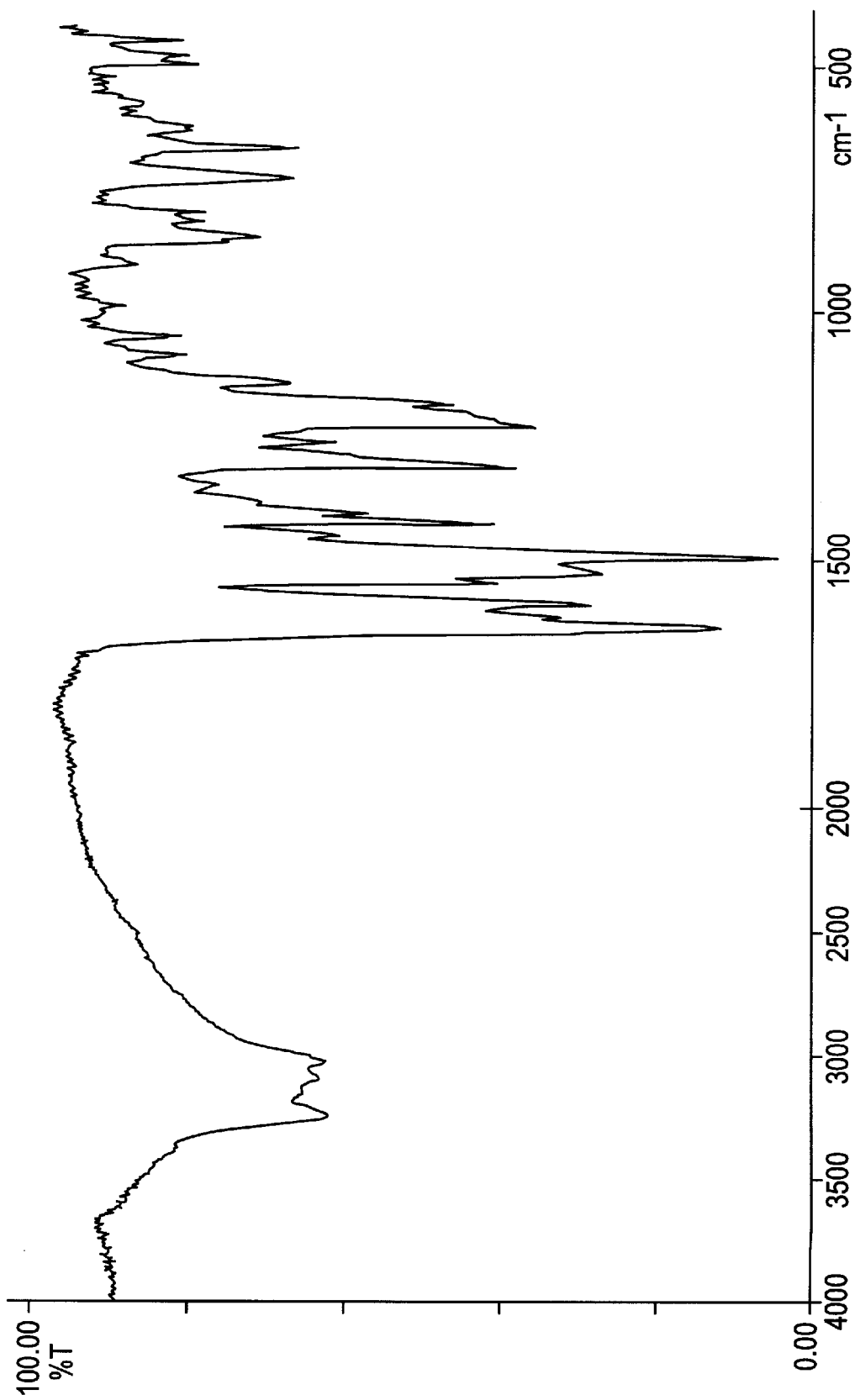
FIG. 11 is an infrared absorption spectrum of the compound obtained in Example 9.
Figure 12:
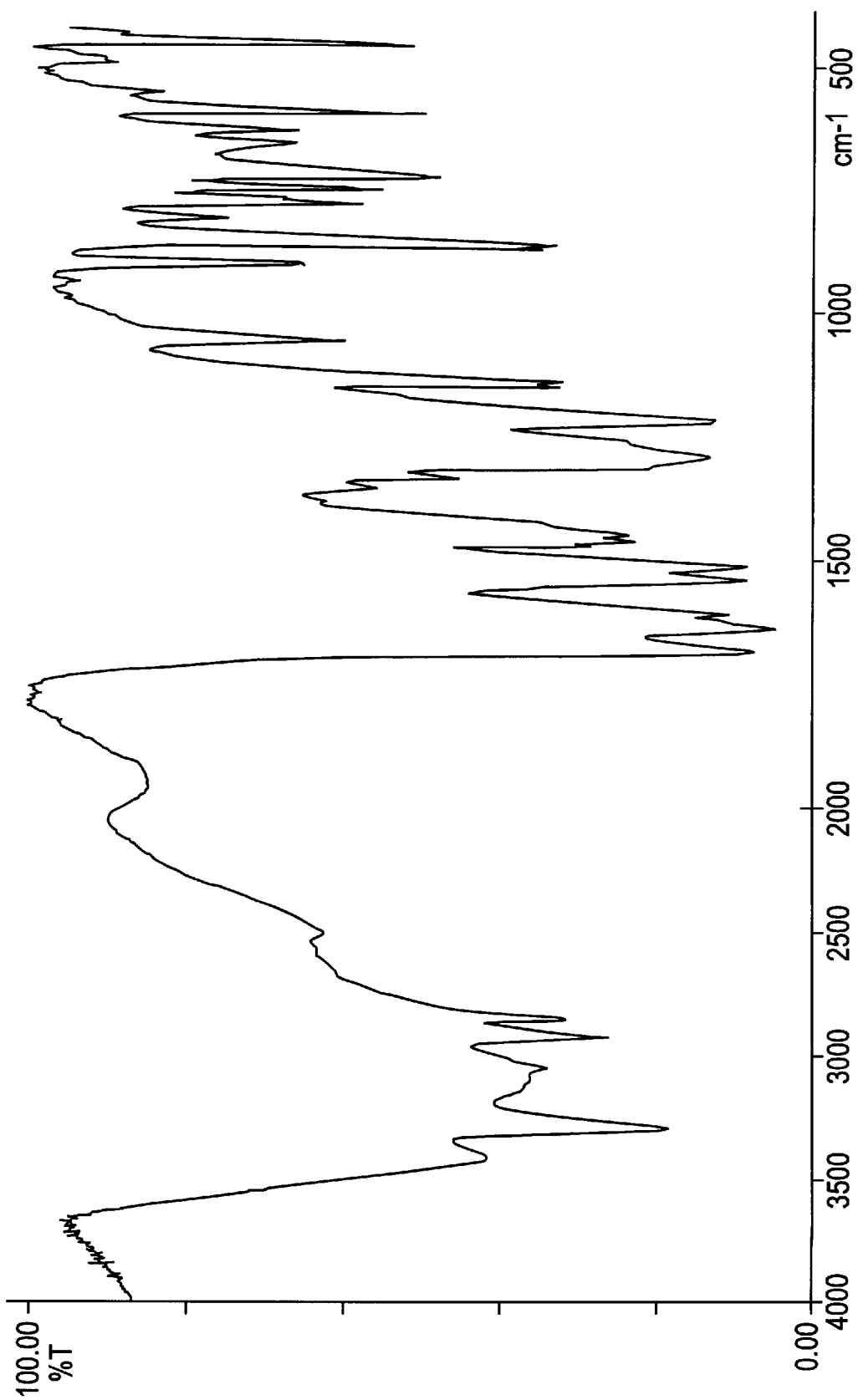
FIG. 12 is an infrared absorption spectrum of the compound obtained in Example 10.
Figure 13:
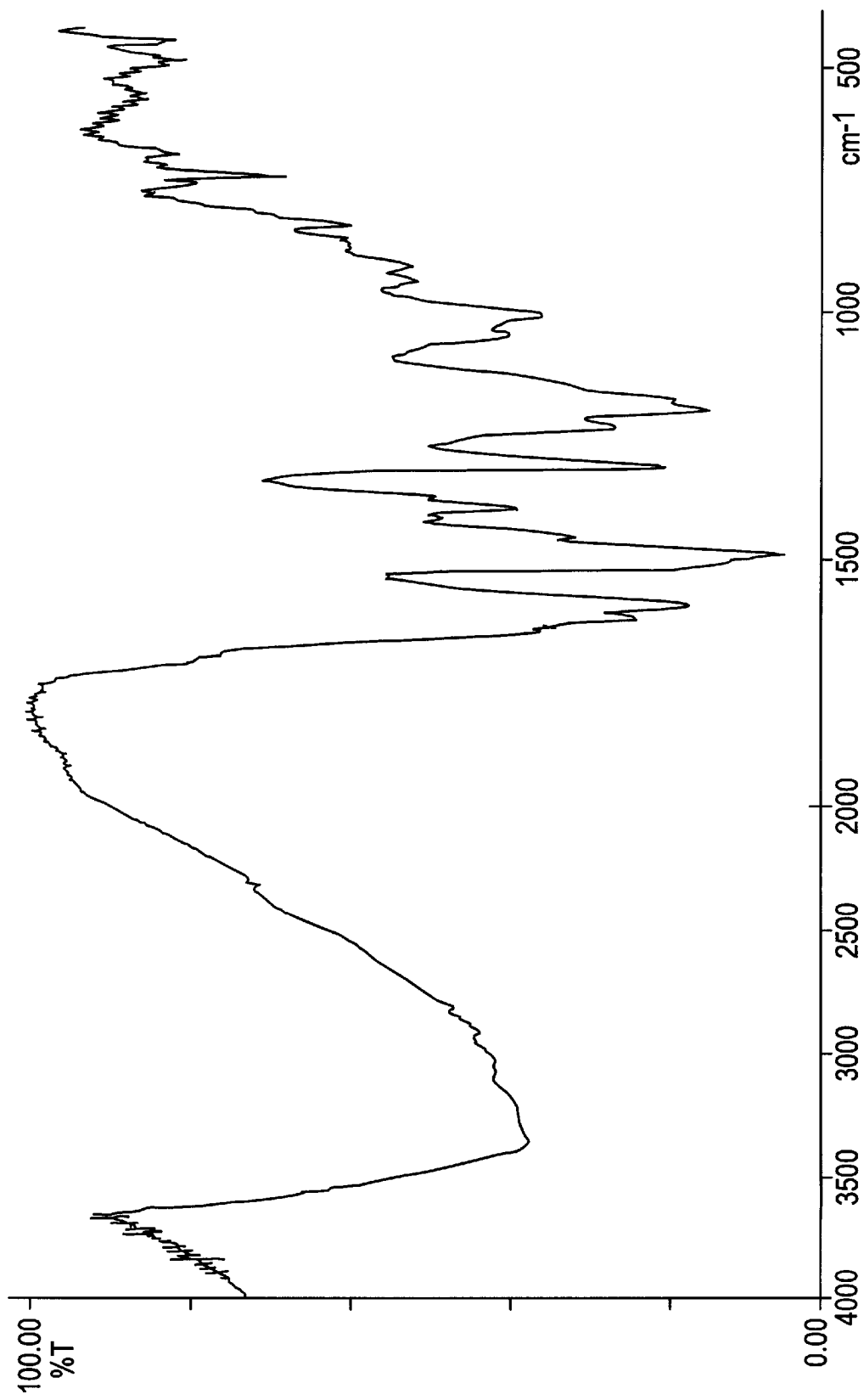
FIG. 13 is an infrared absorption spectrum of the compound obtained in Example 11.
Figure 14:
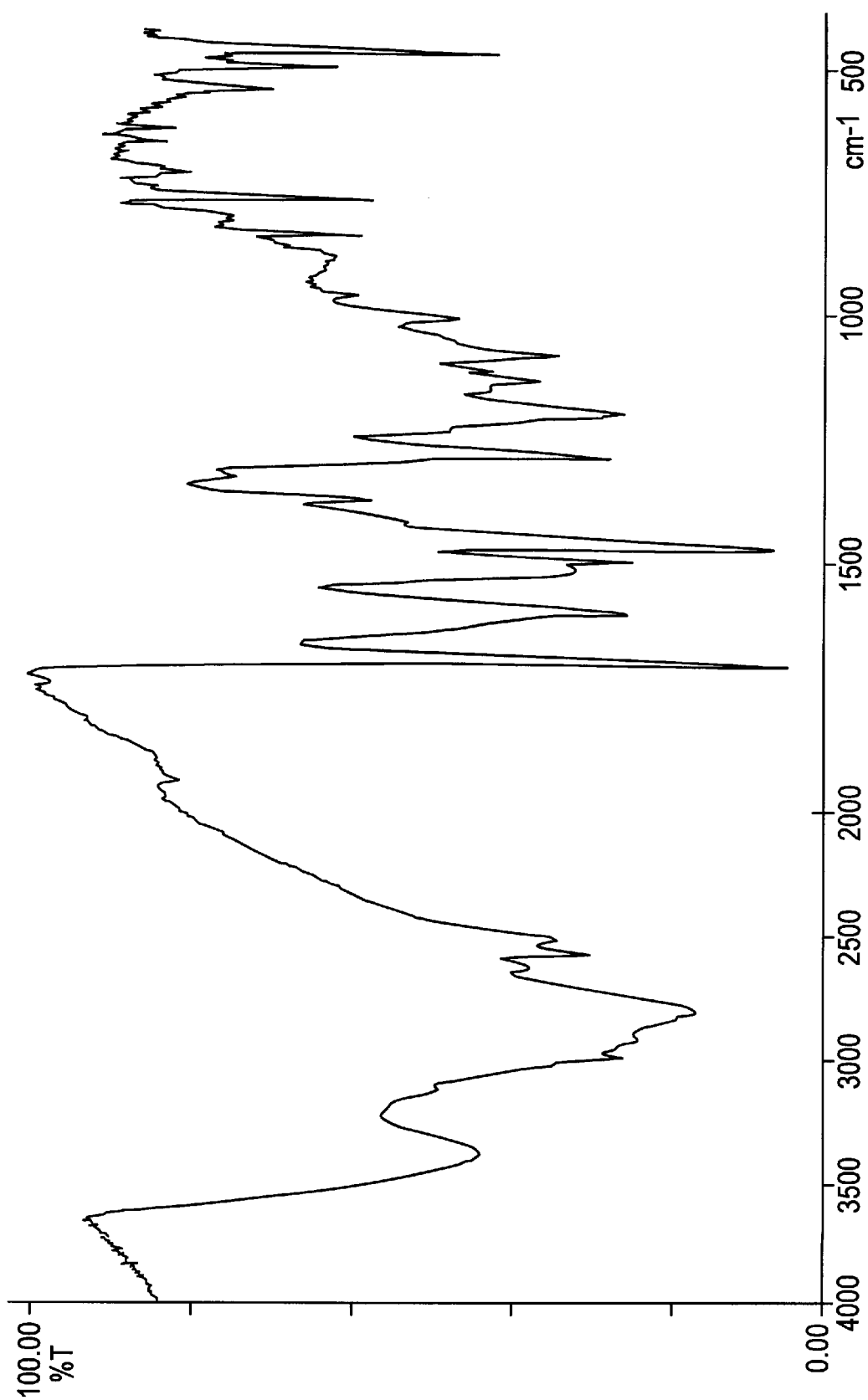
FIG. 14 is an infrared absorption spectrum of the compound obtained in Example 12.
Figure 15:
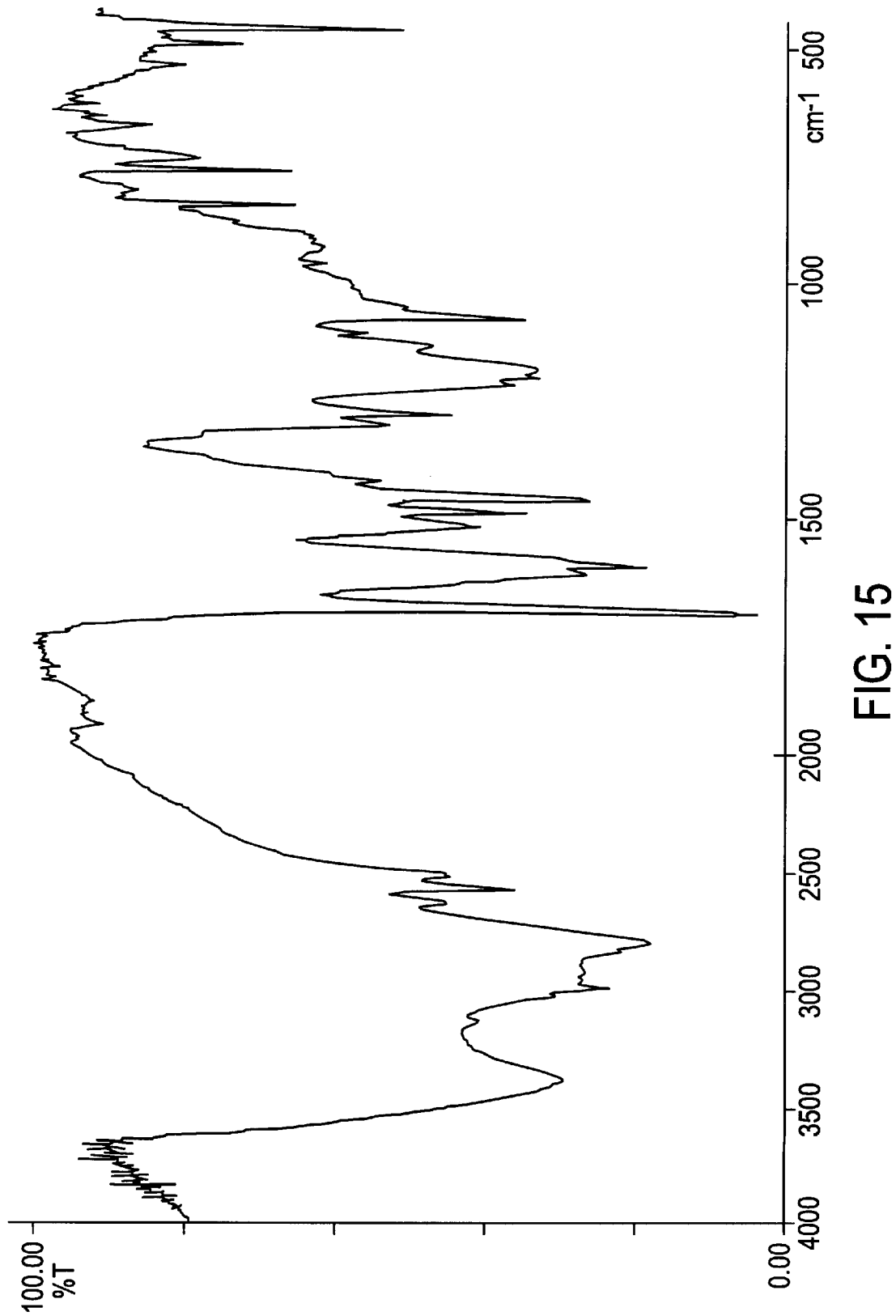
FIG. 15 is an infrared absorption spectrum of the compound obtained in Example 13.
Figure 16:
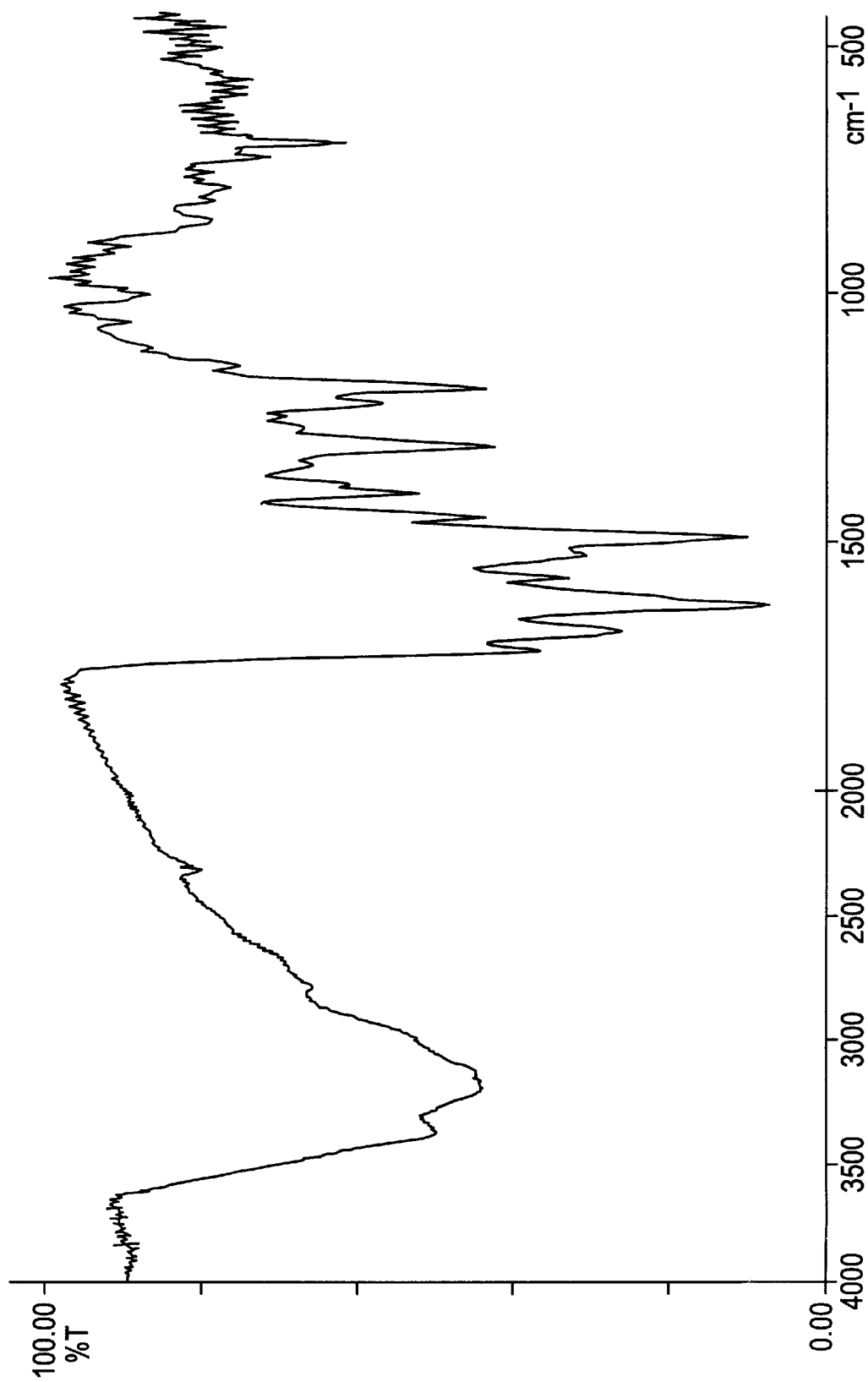
FIG. 16 is an infrared absorption spectrum of the compound obtained in Example 14.

What is claimed is:

1. A bis(aminocarbonylnaphthol)derivative represented by a general formula [I], [II] or [III]:

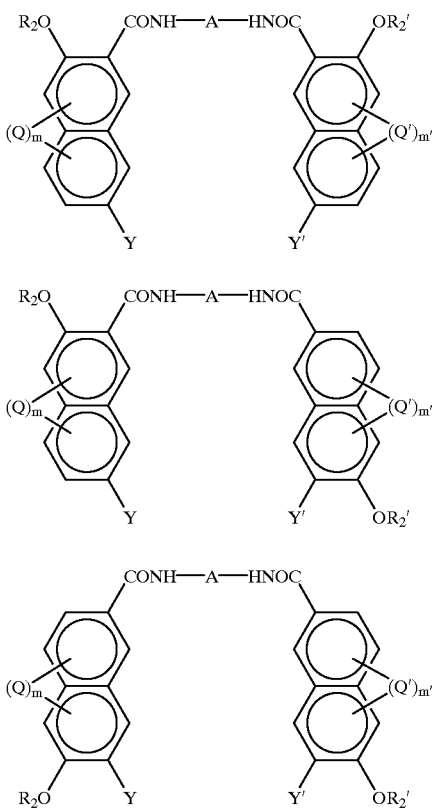

wherein Y represents —(CONH)n—X or —COR;

Y' represents —(CONH)n—X' or —COR';

X and X' may be the same or different and represent an optionally substituted aromatic group or an optionally substituted heterocyclic group having a conjugated double bond;

n represents an integer of 1 or 2;

R and R' may be the same or different and represent a hydroxyl group, an optionally branched alkoxyl group having 1 to 6 carbon atoms, a benzyloxy group, a phenoxy group or a phenacyloxy group;

$R_2$ and $R_2'$ represent a hydrogen atom, an optionally branched alkyl group having 1 to 6 carbon atoms, an optionally branched acyl group having 1 to 6 carbon atoms, or a phenylalkyl group;

Q and Q' represent an optionally branched alkyl group having 1 to 6 carbon atoms, an optionally branched alkoxyl group having 1 to 6 carbon atoms, a halogen atom, a nitro group or a nitroso group;

m and m' represent an integer of 0 to 3; and

A represents an optionally branched alkylene group having 2 to 12 carbon atoms, or a cyclic group having a conjugated double bond.

2. The bis(aminocarbonylnaphthol)derivative according to claim 1, wherein A is an optionally substituted arylene group, or a group selected from the group consisting of the following general formulas [IV] and [VI]:

  [IV]

wherein Ar and Ar' independently represent an optionally substituted aryl group or a heterocyclic group having a conjugated double bond; and M represents a group selected from the group consisting of single bond, —$CH_2$—, —CH=C(E)— (E represents a hydrogen atom, a halogen atom, a lower alkyl group or a cyano group), —O—, —S—, —S—S—, —CO—, —COO—, —$SO_2$—, —N(T)— (T represents an optionally substituted phenyl group or a lower alkyl group), —N=N—, —CH=CH—φ—CH=CH— (φ is an arylene group) and a formula [V]:

  [V]

(wherein G represents —O—, —S— or —NH—)

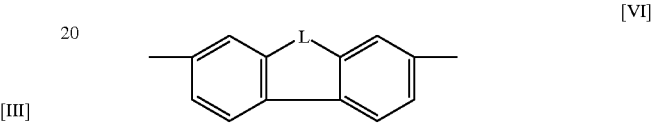  [VI]

wherein L represents >N—$CH_3$, >C=O or >C=S.

3. A process for producing a bis(aminocarbonylnaphthol) derivative represented by the general formula [I],[II] or [III]:

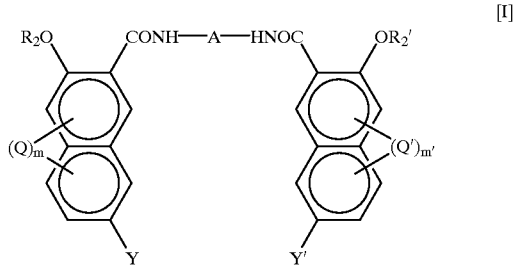  [I]

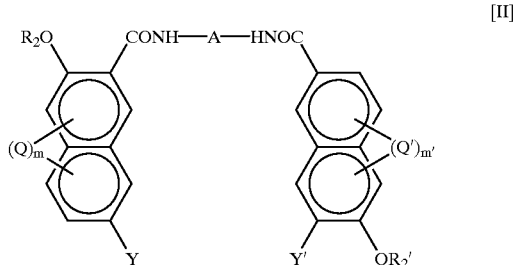  [II]

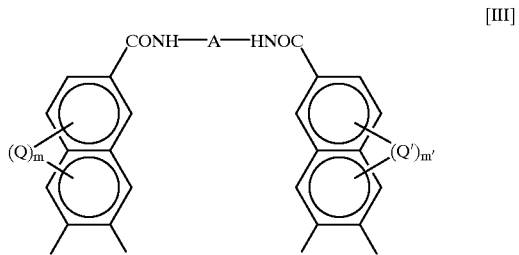  [III]

wherein Y, Y', $R_2$, $R_2'$, Q, Q', m, m' and A are as defined above, which comprises reacting compounds represented by the general formulas [VII], [VII'] and/or [VIII], [VIII']:

[VII]
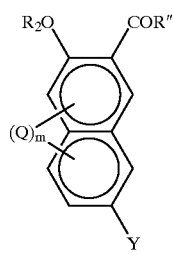

[VII']
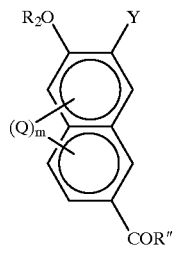

[VIII]
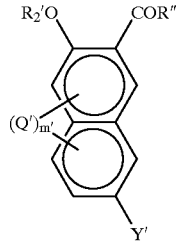

[VIII']
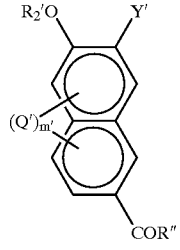

wherein Y, Y', $R_2$, $R_2'$, Q, Q', m, and m' are as defined above; and R" represents a hydroxyl group or a halogen atom with diamines represented by the general formula [IX]:

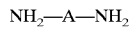     [IX]

wherein A is as defined above.

4. A process for producing a bis(aminocarbonylnaphthol) derivative represented by the general formula [I], [II] or [III]:

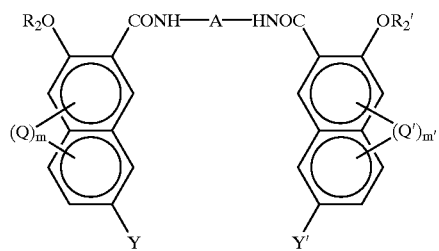     [I]

-continued

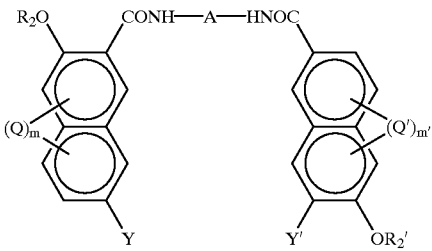     [II]

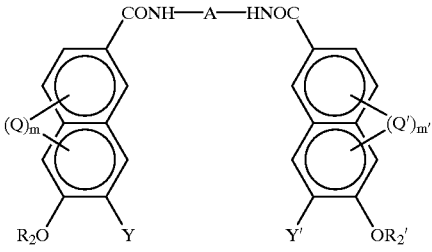     [III]

wherein Y, Y', $R_2$, $R_2'$, Q, Q', m, m' and A are as defined above, which comprises reacting a compound represented by the general formula [VII] or [VII']:

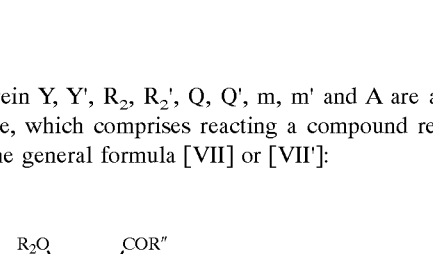     [VII]

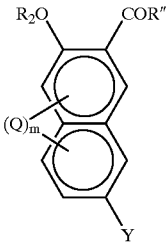

[VII']
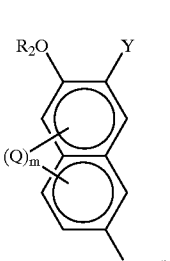

wherein Y, $R_2$, Q and m are as defined above; and R" represents a hydroxyl group or a halogen atom with nitroamines represented by the general formula [X]:

     [X]

wherein A is as defined above, converting the nitro group of the obtained compounds to an amino group to give an amine derivative represented by the general formula [XI] or [XI']:

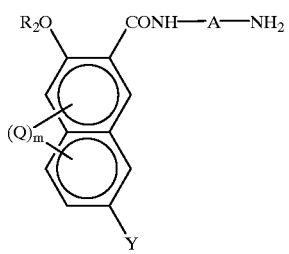 [XI]
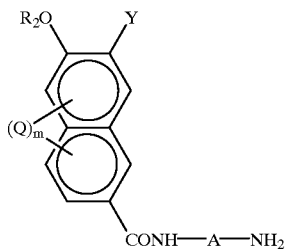 [XI']
wherein Y, $R_2$, Q, m and A are as defined above, and then reacting it with compounds represented by the general formula [VIII] or [VIII']:
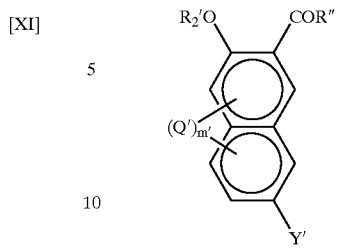 [VIII]
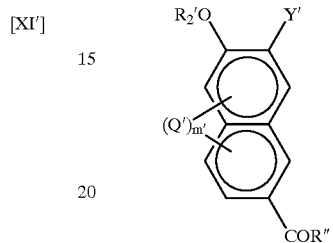 [VIII']
wherein Y', $R_2$', Q' and m' are as defined above; and R" represents a hydroxyl group or a halogen atom.
* * * * *